US009796752B2

(12) United States Patent
Komoriya et al.

(10) Patent No.: US 9,796,752 B2
(45) Date of Patent: Oct. 24, 2017

(54) TERPENOID DERIVATIVES

(71) Applicant: Daiichi Sankyo Company, Limited, Chuo-ku, Tokyo (JP)

(72) Inventors: Satoshi Komoriya, Fujisawa (JP); Yasuhiro Nakagami, Kobe (JP); Emiko Hatano, Urayasu (JP); Takashi Ohnuki, Yamato (JP); Kayoko Masuda, Setagaya-ku (JP); Mayumi Iizuka, Edogawa-ku (JP); Yasunori Ono, Ichikawa (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 14/778,006

(22) PCT Filed: Mar. 18, 2014

(86) PCT No.: PCT/JP2014/057222
§ 371 (c)(1),
(2) Date: Sep. 17, 2015

(87) PCT Pub. No.: WO2014/148455
PCT Pub. Date: Sep. 25, 2014

(65) Prior Publication Data
US 2016/0297849 A1   Oct. 13, 2016

(30) Foreign Application Priority Data

Mar. 19, 2013   (JP) ................. 2013-055887

(51) Int. Cl.
*C07J 71/00* (2006.01)
*C12R 1/785* (2006.01)
*C12P 33/00* (2006.01)
*C12P 33/06* (2006.01)
*C12R 1/645* (2006.01)
*C12P 15/00* (2006.01)
*C12P 17/02* (2006.01)
*C07J 63/00* (2006.01)
*C12N 1/14* (2006.01)
*C12P 33/02* (2006.01)
*C12P 33/20* (2006.01)

(52) U.S. Cl.
CPC .......... *C07J 71/001* (2013.01); *C07J 63/008* (2013.01); *C12N 1/14* (2013.01); *C12P 15/00* (2013.01); *C12P 17/02* (2013.01); *C12P 33/00* (2013.01); *C12P 33/02* (2013.01); *C12P 33/06* (2013.01); *C12P 33/20* (2013.01); *C12R 1/645* (2013.01); *C12R 1/785* (2013.01)

(58) Field of Classification Search
CPC ......... C07J 63/008; C07J 71/001; C12N 1/14; C12P 15/00; C12P 17/02; C12P 33/00; C12P 33/02; C12P 33/06; C12P 33/20; C12R 1/645; C12R 1/785

USPC ....................................... 514/475
See application file for complete search history.

(56) References Cited

U.S. PATENT DOCUMENTS

| 5,451,688 | A | 9/1995 | Kogen | |
| 2007/0172934 | A1* | 7/2007 | Muller | C11B 9/0003 435/148 |
| 2011/0009462 | A1 | 1/2011 | Uhr | |
| 2015/0148384 | A1* | 5/2015 | Anderson | C07J 63/008 514/364 |

FOREIGN PATENT DOCUMENTS

| JP | 6-247894 A | 9/1994 |
| JP | 2001-525665 A | 12/2001 |
| JP | 2011-500754 A | 1/2011 |
| WO | 98/50584 A2 | 11/1998 |
| WO | 99/65478 A1 | 12/1999 |
| WO | 2004/064723 A2 | 8/2004 |
| WO | 2008/064133 A1 | 5/2008 |
| WO | 2009/023232 A1 | 2/2009 |
| WO | 2009/089545 A1 | 7/2009 |
| WO | 2009/129546 A1 | 10/2009 |
| WO | 2009/129548 A1 | 10/2009 |

(Continued)

OTHER PUBLICATIONS

Patani et al. (Chemical Reviews, 1996, 96, 8, 3147-3176).*
Antoniou et al. (Microbiology, 1994, 140, 1633-1640).*
Aleksunes, L.M., et al., "Transcriptional Regulation of Renal Cytoprotective Genes by Nrf2 and Its Potential Use as a Therapeutic Target to Mitigate Cisplatin-Induced Nephrotoxicity," Journal of Pharmacology and Experimental Therapeutics 335(1):2-12, Oct. 2010.
Bataille, A.M., and J.E. Manautou, "Nrf2: A Potential Target for New Therapeutics in Liver Disease," Nature Clinical Pharmacology & Therapeutics 92(3):340-348, Sep. 2012.

(Continued)

*Primary Examiner* — Uma Ramachandran
(74) *Attorney, Agent, or Firm* — Christensen O'Connor Johnson Kindness PLLC

(57) ABSTRACT

It is intended to provide a novel terpenoid derivative that exhibits anti-inflammatory action and a cytoprotective action by activating the Keap1/Nrf2/ARE signaling pathway. The present invention provides terpenoid derivative A represented by the following formula (I):

6 Claims, 12 Drawing Sheets

(56) References Cited

FOREIGN PATENT DOCUMENTS

| WO | 2009/146216 A2 | 12/2009 |
| WO | 2011/130302 A2 | 10/2011 |
| WO | 2012/125488 A1 | 9/2012 |
| WO | 2013/188818 A1 | 12/2013 |

OTHER PUBLICATIONS

Boutten, A., et al., "NRF2 Targeting: A Promising Therapeutic Strategy in Chronic Obstructive Pulmonary Disease," Trends in Molecular Medicine 17(7):363-371, Jul. 2011.

Brennan, L.A., et al., "Oxidative Stress Defense and Repair Systems of the Ocular Lens," Frontiers in Bioscience, Elite Edition 4E(1):141-155, Jan. 2012.

Chapple, S.J., et al., "Crosstalk Between Nrf2 and the Proteasome: Therapeutic Potential of Nrf2 Inducers in Vascular Disease and Aging," International Journal of Biochemistry & Cell Biology 44(8):1315-1320, Aug. 2012.

Cho, H.-Y., and S.R. Kleeberger, "Nrf2 Protects Against Airway Disorders," Toxicology and Applied Pharmacology 244(1):43-56, Apr. 2010. Erratum in: Toxicology and Applied Pharmacology 246(1):186-187, Aug. 2010.

Chowdhry, S., et al., "Loss of Nrf2 Markedly Exacerbates Nonalcoholic Steatohepatitis," Free Radical Biology & Medicine 48(2):357-371, Jan. 2010.

Copple, I.M., "The Keap1-Nrf2 Cell Defense Pathway—A Promising Therapeutic Target?" in G.M. Hawksworth (ed.) vol. 63, "Current Concepts in Drug Metabolism and Toxicology," Advances in Pharmacology, Academic Press, Jun. 2012, pp. 43-79.

Honda, T., et al., "Design and Synthesis of 2-Cyano-3,12-dioxoolean-1,9-dien-28-oic Acid, a Novel and Highly Active Inhibitor of Nitric Oxide Production in Mouse Macrophages," Bioorganic & Medicinal Chemistry Letters 8(19):2711-2714, Oct. 1998.

Honda, T., et al., "A Novel Dicyanotriterpenoid, 2-Cyano-3,12-dioxooleana-1,9(11)-dien-28-onitrile, Active at Picomolar Concentrations for Inhibition of Nitric Oxide Production," Bioorganic & Medicinal Chemistry Letters 12(7):1027-1030, Apr. 2002.

Hybertson, B.M., et al., "Oxidative Stress in Health and Disease: The Therapeutic Potential of Nrf2 Activation," Molecular Aspects of Medicine 32(4-6):234-246, Aug.-Dec. 2011.

International Preliminary Report on Patentability dated Sep. 22, 2015, issued in corresponding International Application No. PCT/JP2014/057222, filed Mar. 18, 2014, 16 pages.

International Search Report dated Jun. 24, 2014, issued in corresponding International Application No. PCT/JP2014/057222, filed Mar. 18, 2014, 7 pages.

Magesh, S., et al., "Small Molecule Modulators of Keap1-Nrf2-ARE Pathway as Potential Preventive and Therapeutic Agents," Medicinal Research Reviews 32(4):687-726, Jul. 2012.

Rojas-Rivera, J., et al., "Antioxidants in Kidney Diseases: The Impact of Bardoxolone Methyl," International Journal of Nephrology, vol. 2012, Article ID 321714, Jun. 2012, 11 pages.

Saha, P.K., et al., "The Triterpenoid 2-Cyano-3,12-dioxooleana-1,9-dien-28-oic-acid Methyl Ester Has Potent Anti-Diabetic Effects in Diet-Induced Diabetic Mice and Lepr(db/db) Mice," Journal of Biological Chemistry 285(52):40581-40592, Dec. 2010.

Sussan, T.E., et al., "Targeting Nrf2 With the Triterpenoid CDDO-Imidazolide Attenuates Cigarette Smoke-Induced Emphysema and Cardiac Dysfunction in Mice," Proceedings of the National Academy of Sciences of the USA (PNAS) 106(1):250-255, Jan. 2009.

Vomhof-DeKrey, E.E., et al., "The Nrf2-Antioxidant Response Element Pathway: A Target for Regulating Energy Metabolism," Journal of Nutritional Biochemistry 23(10):1201-1206, Oct. 2012.

Wei, Y., et al., "Nrf2 Has a Protective Role Against Neuronal and Capillary Degeneration in Retinal Ischemia-Reperfusion Injury," Free Radical Biology & Medicine 51(1):216-224, Jul. 2011.

Yadav, U.C.S., et al., "Emerging Role of Antioxidants in the Protection of Uveitis Complications," Current Medicinal Chemistry 18(6):931-942, Feb. 2011.

Extended European Search Report dated Aug. 22, 2016, issued in European Patent Application No. 14 77 0519.8, filed Sep. 17, 2015, 10 pages.

Fragrance Journal, "[Feature] Oxidative Stress and Its Defense" (Abstract), No. 392, vol. 41, No. 2, May 2013, published Feb. 15, 2013, <https://translate.googleusercontent.com/translate_c?depth=1&hl=en&prev=search&rurl=translate.google.co.uk&sl=ja&u=http://www.fragrance-j.co.jp/book/b209965.html&usg=ALKJrhi3KQOVbIJOijGHQ8mEkz9xnZJbRg [retrieved Aug. 10, 2016], 3 pages.

Gautam, R., and S.M. Jachak, "Recent Developments in Anti-Inflammatory Natural Products," Medicinal Research Reviews 29(5):767-820, Sep. 2009.

Katayama, S., "Soyasaponins Mediate Antioxidative Stress Activity via the Nrf2-ARE Pathway," Fragrance Journal 41(2):57-63, May 2013; Database CA [Online], Chemical Abstracts Service, Columbus, Ohio, HCAplus Accession No. 2013:372298, 5 pages.

* cited by examiner

TERPENOID DERIVATIVES

TECHNICAL FIELD

The present invention relates to a terpenoid derivative that has the ability to activate the Keap1/Nrf2/ARE signaling pathway and is excellent in anti-inflammatory action and cytoprotective action.

BACKGROUND ART

Upon detection of active oxygen species, etc., generated in the course of energy metabolism, host defense systems such as antioxidative enzyme groups, detoxification metabolism enzyme groups or the like are initiated. The Keap1/Nrf2/ARE signaling pathway controls the initiation of this host defense system.

It is known that the activation of the Keap1/Nrf2/ARE signaling pathway induces its target gene of NAD(P)H: quinone oxidoreductase-1 (NQO1), heme oxygenase-1 (HO-1), γ-glutamate cysteine ligase catalytic subunit (GCLC), or the like (Non-patent Literature 1). NQO1 is a phase 2 enzyme of xenobiotic metabolism and is important for detoxification. HO-1 and GCLC are known as typical antioxidative enzymes. When these enzymes are increased in amount or activated, the cells become resistant to poison, oxidative stress, inflammation, etc. Compounds that activate this signaling pathway are therefore considered to serve as therapeutic drugs for various diseases (Non-patent Literatures 2 to 5). Specific examples of the targeted diseases are as given below.

Nrf2-deficient mice have been reported to exhibit vulnerability in the retinal ischemia/reperfusion system (Non-patent Literature 6). This suggests the applicability to the compounds to eye diseases such as allergic conjunctival disease, viral conjunctivitis, pterygium, corneal infection, corneal endothelial disorder, uveitis, Behcet's disease, diabetic retinopathy, retinal detachment, retinal vein occlusion, central serous chorioretinopathy, age-related macular degeneration, diabetic macular edema, macular disease, retinitis pigmentosa, glaucoma, and cataract (Non-patent Literatures 7 and 8).

Nrf2-deficient mice have been reported to exhibit vulnerability to cisplatin-induced nephrotoxicity (Non-patent Literature 9). This suggests the applicability of the compounds to renal diseases such as acute nephritis, chronic nephritis, acute renal failure, chronic renal failure, nephrotic syndrome, IgA nephropathy, diabetic nephropathy, gouty kidney, nephrosclerosis, hydronephrosis, tubulointerstitial nephritis, and urinary tract infection (Non-patent Literature 10).

Nrf2-deficient mice have been reported to exhibit vulnerability to cigarette smoke exposure (Non Patent Literature 11). This suggests the applicability of the compounds to respiratory diseases such as bronchitis, pneumonia, pleuritis, chronic obstructive pulmonary disease, diffuse panbronchiolitis, pulmonary emphysema, and asthma (Non-patent Literatures 12 and 13). Nrf2-deficient mice have been reported to be likely to develop non-alcoholic steatohepatitis when fed with methionine/choline-deficient diet (Non-patent Literature 14). This suggests the applicability of the compounds to hepatic diseases such as alcoholic fatty liver, non-alcoholic steatohepatitis, hepatic fibrosis, and liver cirrhosis (Non-patent Literatures 2 and 15).

Also, Nrf2 activators have been reported to exhibit hypoglycemic action in mice (Non-patent Literature 16). This suggests the applicability of the compounds to diabetes mellitus and its complications (diabetic retinopathy, diabetic nephropathy, and diabetic neuropathy) or the like.

As substances that activate the Keap1/Nrf2/ARE signaling pathway, sulforaphane contained in broccoli sprouts, curcumin contained in turmeric for curry, or the like have been reported to activate Nrf2 and promote the detoxification of carcinogens (Non-patent Literature 17). Also, a 5-membered ring triterpenoid comprising methyl 2-cyano-3,12-dioxooleana-1,9(11)-dien-28-acid (Non-patent Literature 18 and Patent Literatures 1 to 9) discovered by Honda et al. has been reported to activate the Keap1/Nrf2/ARE signaling pathway. These compounds have been reported to bring about the production of several anti-inflammatory proteins and antioxidative proteins (e.g., NQO1, HO-1, and GCLC) (Patent Literature 9).

CITATION LIST

Patent Literature

Patent Literature 1: WO9965478
Patent Literature 2: WO2012125488
Patent Literature 3: WO2011130302
Patent Literature 4: WO2009146216
Patent Literature 5: WO2009129546
Patent Literature 6: WO2009129548
Patent Literature 7: WO2009023232
Patent Literature 8: WO2004064723
Patent Literature 9: WO2009089545

Non-Patent Literature

Non-patent Literature 1: Int. J. Biochem. Cell. Biol. 2012; 44: 1315-1320
Non-patent Literature 2: Clin. Pharmacol. Ther. 2012; 92: 340-348
Non-patent Literature 3: Adv. Pharmacol. 2012; 63: 43-79
Non-patent Literature 4: Med. Res. Rev. 2012; 32: 687-726
Non-patent Literature 5: Mol. Aspects. Med. 2011; 32: 234-246
Non-patent Literature 6: Free Radic Biol. Med. 2011; 51: 216-224
Non-patent Literature 7: Front Biosci. (Elite Ed.) 2012; 4: 141-155
Non-patent Literature 8: Curr. Med. Chem. 2011; 18: 931-942
Non-patent Literature 9: J. Pharmacol. Exp. Ther. 2010; 335: 2-12
Non-patent Literature 10: Int. J. Nephrol. 2012; 321714
Non-patent Literature 11: Proc. Natl. Acad. Sci. USA 2009; 106: 250-255
Non-patent Literature 12: Trends Mol. Med. 2011; 17: 363-371
Non-patent Literature 13: Toxicol. Appl. Pharmacol. 2010; 244: 43-56
Non-patent Literature 14: Free Radic Biol. Med. 2010; 48: 357-371
Non-patent Literature 15: J. Nutr. Biochem. 2012; 23: 1201-1206
Non-patent Literature 16: J. Biol. Chem. 2010; 285: 40581-40592
Non-patent Literature 17: The Journal of The Japanese Biochemical Society, 2009; 81: 447-9
Non-patent Literature 18: Bioorg. Med. Chem. Lett., 1998: 8: 2711-2714

SUMMARY OF INVENTION

Technical Problem

The present inventors have conducted diligent studies on compounds that activate the Keap1/Nrf2/ARE signaling pathway, and consequently completed the present invention by finding that a specific terpenoid derivative has an excellent anti-inflammatory action and cytoprotective action.

Solution to Problem

Specifically, the present invention provides (1) a terpenoid derivative represented by the following formula (I):

[Formula 1]

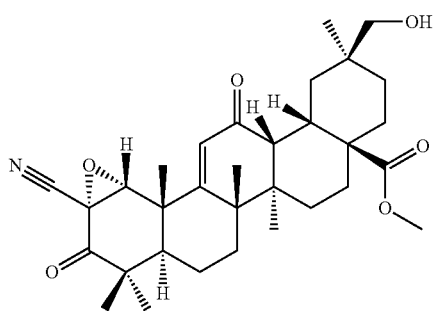

(2) a terpenoid derivative having the following physico-chemical properties:
1) appearance: a colorless powdery substance
2) molecular formula: $C_{32}H_{43}NO_6$
3) molecular weight: 537 (measured by ESI mass spectrometry)
4) the accurate mass, $[M+H]^+$, measured by high-resolution LC-ESI mass spectrometry is as given below:
   found: 538.31549
   calculated: 538.31631
5) $^1$H-nuclear magnetic resonance spectra: the $^1$H-nuclear magnetic resonance spectra (500 MHz) measured with the signal of TMS defined as 0.00 ppm in deuterated chloroform are as given below:
   σ: 0.92 (3H, s), 1.08 (3H, s), 1.12 (3H, s), 1.14-1.17 (1H, m), 1.19 (3H, s), 1.22-1.24 (1H, m), 1.18-1.25 (1H, m), 1.28 (3H, s), 1.28 (3H, s), 1.46-1.48 (1H, m), 1.48-1.52 (1H, m), 1.50-1.54 (1H, m), 1.59-1.67 (2H, m), 1.62-1.66 (1H, m), 1.64-1.67 (1H, m), 1.75 (1H, d, J=13.5 Hz), 1.80-1.83 (1H, m), 1.85-1.87 (2H, m), 1.98 (1H, dd, J=9.0 Hz, 4.5 Hz), 2.95 (1H, s), 2.98 (1H, brs), 3.45 (1H, d, J=11.5 Hz), 3.70 (3H, s), 3.73 (1H, d, J 11.5 Hz), 4.34 (1H, s), 6.11 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
   σ: 18.5 (t), 21.1 (q), 21.6 (q), 23.0 (q), 24.0 (q), 24.1 (t), 27.3 (q), 28.2 (q), 28.6 (t), 29.6 (t), 31.0 (d), 31.5 (t), 31.6 (t), 32.4 (t), 35.7 (s), 41.2 (s), 42.3 (s), 42.8 (d), 45.3 (s), 45.8 (s), 47.1 (s), 49.6 (d), 52.3 (q), 53.5 (s), 67.6 (t), 69.3 (d), 113.7 (s), 124.8 (d), 169.8 (s), 178.0 (s), 199.6 (s), 202.5 (s) ppm 7) high-performance liquid chromatography:
column: Unison UK-C18
   (4.6 mm in diameter×75 mm in length; manufactured by Imtakt Corp.)
Solvent:
   A: 10 mM aqueous ammonium formate solution containing 0.01% formic acid
   B: acetonitrile containing 0.01% formic acid
   A/B=45/55 isocratic
flow rate: 1.0 ml/min
temperature: 40° C.
detection: ultraviolet absorption λ230 nm
retention time: 5.8 minutes, (3) a terpenoid derivative represented by the following formula (II):

[Formula 2]

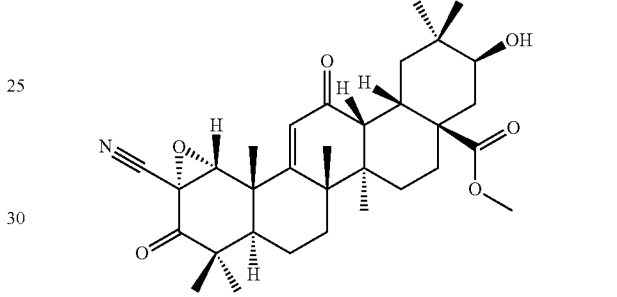

(4) a terpenoid derivative having the following physico-chemical properties:
1) appearance: a colorless powdery substance
2) molecular formula: $C_{32}H_{43}NO_6$
3) molecular weight: 537 (measured by ESI mass spectrometry)
4) the accurate mass, $[M+H]^+$, measured by high-resolution LC-ESI mass spectrometry is as given below:
   found: 538.31573
   calculated: 538.31631
5) $^1$H-nuclear magnetic resonance spectra: the $^1$H-nuclear magnetic resonance spectra (500 MHz) measured with the signal of TMS defined as 0.00 ppm in deuterated chloroform are as given below:
   σ: 0.99 (3H, s), 0.99 (3H, s), 1.06 (3H, s), 1.12 (3H, s), 1.19 (3H, s), 1.19-1.22 (1H, m), 1.27 (3H, s), 1.27 (3H, s), 1.29-1.35 (2H, m), 1.45-1.49 (1H, m), 1.62-1.66 (1H, m), 1.58-1.67 (2H, m), 1.64-1.69 (1H, m), 1.72-1.75 (1H, m), 1.69-1.79 (1H, m), 1.88 (2H, dd, J=10.0 Hz, 3.0 Hz), 1.96 (1H, dd, J=10.0 Hz, 4.5 Hz), 2.97 (1H, s), 3.04 (1H, dd, J=10.0 Hz, 4.5 Hz), 3.49 (1H, dd, J=11.5 Hz, 5.0 Hz), 3.70 (3H, s), 4.34 (1H, s), 6.08 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
   σ: 16.6 (q), 18.5 (t), 21.6 (q×2), 23.0 (q), 24.0 (q), 24.1 (t), 28.2 (q), 28.4 (t), 29.3 (q), 31.3 (d), 31.6 (d), 36.1 (t), 36.2 (s), 40.4 (t), 41.1 (s), 42.2 (s), 42.8 (d), 45.3 (s), 45.8 (s), 49.1 (s), 49.3 (d), 52.3 (s), 53.4 (s), 69.2 (d), 73.9 (t), 113.7 (s), 125.0 (d), 168.9 (s), 176.8 (s), 198.9 (s), 202.5 (s) ppm 7) high-performance liquid chromatography:
column: Unison UK-C18
(4.6 mm in diameter×75 mm in length; manufactured by Imtakt Corp.)
Solvent:
   A: 10 mM aqueous ammonium formate solution containing 0.01% formic acid
   B: acetonitrile containing 0.01% formic acid
   A/B=45/55 isocratic
flow rate: 1.0 ml/min
temperature: 40° C.
detection: ultraviolet absorption λ230 nm
retention time: 3.8 minutes,
(5) a terpenoid derivative represented by the following formula (III):

[Formula 3]

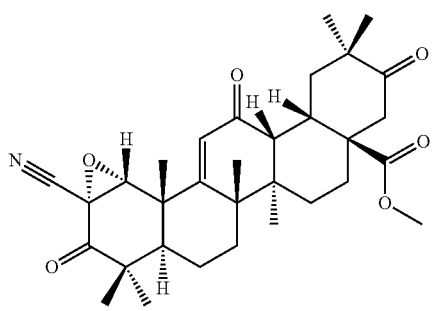

(III)

(6) a terpenoid derivative having the following physicochemical properties:
1) appearance: a colorless powdery substance
2) molecular formula: $C_{32}H_{41}NO_6$
3) molecular weight: 535 (measured by ESI mass spectrometry)
4) the accurate mass, $[M+H]^+$, measured by high-resolution LC-ESI mass spectrometry is as given below:
   found: 536.30023
   calculated: 536.30066
5) $^1$H-nuclear magnetic resonance spectra: the $^1$H-nuclear magnetic resonance spectra (500 MHz) measured with the signal of TMS defined as 0.00 ppm in deuterated chloroform are as given below:
   σ: 1.04 (3H, s), 1.05 (3H, s), 1.13 (3H, s), 1.19 (3H, s), 1.20-1.26 (1H, m), 1.30 (m, 3H), 1.29 (3H, s), 1.33 (3H, s), 1.47-1.50 (1H, m), 1.63-1.68 (2H, m), 1.59-1.68 (2H, m), 1.65-1.67 (1H, m), 1.64-1.73 (2H, m), 1.71 (1H, d, J=13.5 Hz), 1.98 (1H, d, J=13.5 Hz), 2.03 (1H, dd, J=14.0 Hz, 3.5 Hz), 2.27 (1H, d, J=14.5 Hz), 2.85 (1H, d, J=14.5 Hz), 3.05 (1H, d, J=4.5 Hz), 3.38 (1H, brd, J=13.5 Hz), 3.74 (3H, s), 4.34 (1H, s), 6.12 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
   σ: 18.4 (t), 21.6 (q×2), 23.0 (q), 24.1 (q×2), 25.5 (q), 25.6 (t), 28.2 (q), 28.3 (t), 31.5 (t), 31.7 (d), 37.4 (t), 41.2 (s), 42.1 (s), 42.8 (d), 45.3 (s), 46.6 (s), 45.9 (s), 47.0 (t), 49.1 (d), 51.1 (s), 52.7 (q), 53.4 (s), 69.2 (d), 113.7 (s), 124.8 (d), 169.4 (s), 175.5 (s), 198.5 (s), 202.4 (s), 213.4 (s) ppm 7) high-performance liquid chromatography:
column: Unison UK-C18
(4.6 mm in diameter×75 mm in length; manufactured by Imtakt Corp.)
Solvent:
   A: 10 mM aqueous ammonium formate solution containing 0.01% formic acid
   B: acetonitrile containing 0.01% formic acid
   A/B=45/55 isocratic
flow rate: 1.0 ml/min
temperature: 40° C.
detection: ultraviolet absorption λ230 nm
retention time: 6.2 minutes,
(7) a terpenoid derivative represented by the following formula (IV):

[Formula 4]

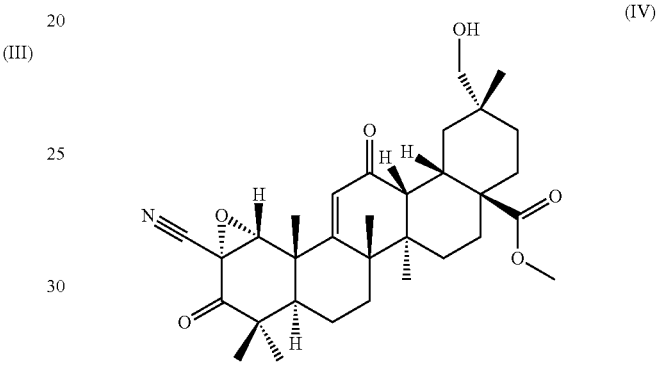

(IV)

(8) a terpenoid derivative having the following physicochemical properties:
1) appearance: a colorless powdery substance
2) molecular formula: $C_{32}H_{43}NO_6$
3) molecular weight: 537 (measured by ESI mass spectrometry)
4) the accurate mass, $[M+H]^+$, measured by high-resolution LC-ESI mass spectrometry is as given below:
   found: 538.31592
   calculated: 538.31631
5) $^1$H-nuclear magnetic resonance spectra: the $^1$H-nuclear magnetic resonance spectra (500 MHz) measured with the signal of TMS defined as 0.00 ppm in deuterated chloroform are as given below:
   σ: 1.05 (3H, s), 1.11 (3H, s), 1.15 (3H, s), 1.22 (3H, s), 1.25-1.27 (1H, m), 1.27-1.29 (1H, m), 1.30 (3H, s), 1.30 (3H, s), 1.40 (1H, brt, J=13.0 Hz), 1.48-1.52 (1H, m), 1.50-1.54 (1H, m), 1.58-1.60 (1H, m), 1.60-1.63 (1H, m), 1.62-1.71 (2H, m), 1.66-1.70 (1H, m), 1.69-1.73 (1H, m), 1.76-1.82 (1H, m), 1.90-1.94 (1H, m), 1.93-1.99 (1H, m), 2.01 (1H, dd, J=4.5 Hz, 10.0 Hz), 3.02 (1H, d, J=4.5 Hz), 3.12 (1H, dt, J=3.5 Hz, 13.5 Hz), 3.32 (3H, s), 3.74 (3H, s), 4.36 (1H, s), 6.11 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
   σ: 18.3 (t), 18.7 (q), 21.4 (q), 21.5 (q), 22.7 (t), 22.8 (q), 23.9 (q), 28.0 (q), 28.2 (t), 28.7 (t), 30.1 (t), 30.8 (d), 31.4 (t), 32.0 (t), 35.8 (s), 40.9 (s), 42.0 (s), 42.5 (d), 45.1 (s), 45.6 (s), 47.4 (s), 49.6 (d), 52.0 (q), 53.2 (s), 69.1 (d), 74.2 (t), 113.6 (s), 124.8 (d), 168.7 (s), 178.0 (s), 198.7 (s), 202.4 (s) ppm 7) high-performance liquid chromatography:
column: Unison UK-C18
(4.6 mm in diameter×75 mm in length; manufactured by Imtakt Corp.)
Solvent:
A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
temperature: 40° C.
detection: ultraviolet absorption λ230 nm
retention time: 5.2 minutes,
(9) a terpenoid derivative represented by the following formula (V):

[Formula 5]

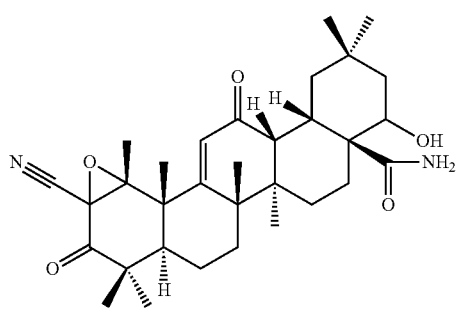

(V)

(10) a terpenoid derivative having the following physicochemical properties:
1) appearance: a colorless powdery substance
2) molecular formula: $C_{31}H_{42}N_2O_5$
3) molecular weight: 522 (measured by ESI mass spectrometry)
4) the accurate mass, $[M+H]^+$, measured by high-resolution LC-ESI mass spectrometry is as given below:
found: 523.31616
calculated: 523.31665
5) $^1$H-nuclear magnetic resonance spectra: the $^1$H-nuclear magnetic resonance spectra (500 MHz) measured with the signal of TMS defined as 0.00 ppm in deuterated chloroform are as given below:
σ: 0.95 (3H, s), 1.03 (3H, s), 1.10 (3H, s), 1.13 (3H, s), 1.19 (3H, s), 1.26-1.30 (1H, m), 1.28-1.30 (1H, m), 1.28 (3H, s), 1.34 (3H, s), 1.35 (1H, t, J=12.5 Hz), 1.48-1.52 (1H, m), 1.57-1.60 (1H, m), 1.60-1.68 (2H, m), 1.64-1.68 (1H, m), 1.65-1.69 (1H, m), 1.72-1.74 (1H, m), 1.79-1.81 (1H, m), 1.97-1.99 (1H, m), 1.98-2.00 (1H, m), 2.92 (1H, brd, J=13.0 Hz), 3.42 (1H, d, J=4.0 Hz), 3.90 (1H, brd, J=10.0 Hz), 4.34 (1H, s), 6.08 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
σ: 17.4 (t), 18.3 (t), 21.4 (q), 21.5 (q), 22.8 (q), 24.0 (q), 24.2 (q), 27.7 (t), 28.0 (q), 31.1 (s), 31.4 (t), 31.8 (d), 33.2 (q), 35.6 (t), 40.9 (s), 42.58 (d), 42.62 (s), 43.8 (t), 45.1 (s), 45.8 (s), 49.2 (d), 51.6 (s), 53.3 (s), 69.1 (d), 71.0 (d), 113.6 (s), 124.8 (d), 168.7 (s), 178.7 (s), 198.8 (s), 202.3 (s) ppm 7) high-performance liquid chromatography:
column: Unison UK-C18
(4.6 mm in diameter×75 mm in length; manufactured by Imtakt Corp.)
Solvent:
A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
temperature: 40° C.
detection: ultraviolet absorption λ230 nm
retention time: 3.2 minutes,
(11) a terpenoid derivative represented by the following formula (VI):

[Formula 6]

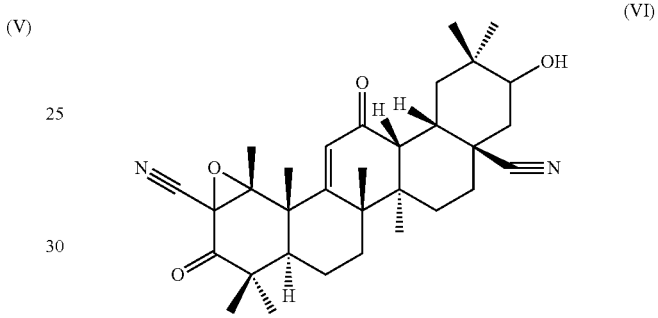

(VI)

(12) a terpenoid derivative having the following physicochemical properties:
1) appearance: a colorless powdery substance
2) molecular formula: $C_{31}H_{40}N_2O_4$
3) molecular weight: 504 (measured by ESI mass spectrometry)
4) the accurate mass, $[M+H]^+$, measured by high-resolution LC-ESI mass spectrometry is as given below:
found: 505.30551
calculated: 505.30608
5) $^1$H-nuclear magnetic resonance spectra: the $^1$H-nuclear magnetic resonance spectra (500 MHz) measured with the signal of TMS defined as 0.00 ppm in deuterated chloroform are as given below:
σ: 0.998 (3H, s), 1.001 (3H, s), 1.06 (3H, s), 1.14 (3H, s), 1.20 (3H, s), 1.30 (1H, t, J=13.5 Hz), 1.32 (3H, s), 1.36 (1H, dt, J=3.5 Hz, 12.5 Hz), 1.50 (3H, s), 1.54-1.58 (1H, m), 1.64-1.69 (1H, m), 1.68-1.70 (2H, m), 1.70-1.73 (1H, m), 1.74 (1H, dd, J=3.5 Hz, 13.5 Hz), 1.97-2.01 (1H, m), 2.00-2.03 (1H, m), 1.99-2.11 (2H, m), 2.07 (1H, brt, J=13.5 Hz), 2.80 (1H, dt, J=3.5 Hz, 13.5 Hz), 3.26 (1H, d, J=5.0 Hz), 3.45 (1H, dd, J=5.0 Hz, 12.0 Hz), 4.34 (1H, s), 6.14 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
σ: 16.3 (q), 18.2 (t), 21.36 (q), 21.38 (q), 22.8 (q), 24.3 (q), 25.1 (t), 28.0 (q), 28.3 (t), 29.0 (q), 31.4 (t), 33.7 (d), 35.0 (t), 35.9 (s), 39.5 (t), 39.7 (s), 41.0 (s), 42.1 (s), 42.5 (s), 45.1 (s), 45.8 (s), 49.3 (d), 53.2 (s), 68.9 (d), 72.4 (d), 113.5 (s), 123.5 (s), 124.5 (d), 169.6 (s), 197.5 (s), 202.1 (s) ppm 7) high-performance liquid chromatography:
column: Unison UK-C18
(4.6 mm in diameter×75 mm in length; manufactured by Imtakt Corp.)
Solvent:
A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
temperature: 40° C.
detection: ultraviolet absorption λ230 nm
retention time: 4.2 minutes,

(13) a terpenoid derivative represented by the following formula (VII):

[Formula 7]

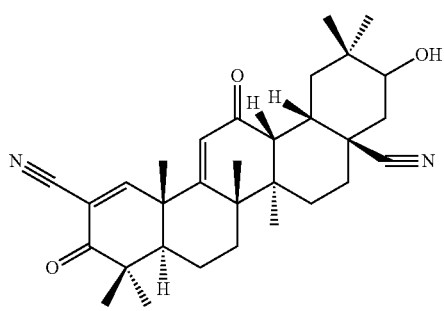

(VII)

(14) a terpenoid derivative having the following physicochemical properties:
1) appearance: a colorless powdery substance
2) molecular formula: $C_{31}H_{40}N_2O_3$
3) molecular weight: 488 (measured by ESI mass spectrometry)
4) the accurate mass, $[M+H]^+$, measured by high-resolution LC-ESI mass spectrometry is as given below:
found: 489.31073
calculated: 489.31117
5) $^1$H-nuclear magnetic resonance spectra: the $^1$H-nuclear magnetic resonance spectra (500 MHz) measured with the signal of TMS defined as 0.00 ppm in deuterated chloroform are as given below:
σ: 0.996 (3H, s), 0.997 (3H, s), 0.998 (3H, s), 1.19 (3H, s), 1.27 (3H, s), 1.28 (1H, t, J=14.0 Hz), 1.36 (1H, dt, J=2.5 Hz, 13.0 Hz), 1.53 (3H, s), 1.56 (3H, s), 1.60-1.64 (1H, m), 1.63-1.69 (1H, m), 1.70-1.74 (1H, m), 1.71 (1H, dd, J=3.5 Hz, 14.0 Hz), 1.78 (1H, dd, J=3.0 Hz, 11.0 Hz), 1.82-1.86 (2H, m), 1.99-2.02 (1H, m), 1.99-2.10 (2H, m), 2.08 (1H, brt, J=12.0 Hz), 2.79 (1H, dt, J=3.5 Hz, 13.5 Hz), 3.25 (1H, d, J=5.0 Hz), 3.45 (1H, dd, J=5.0 Hz, 11.5 Hz), 6.02 (1H, s), 8.03 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
σ: 16.3 (q), 18.2 (t), 21.4 (q), 21.5 (q), 24.9 (q), 25.1 (t), 26.7 (q), 27.0 (q), 28.1 (t), 29.0 (q), 31.7 (t), 33.6 (d), 34.9 (t), 35.9 (s), 39.5 (t), 39.6 (s), 42.1 (s), 42.6 (s), 45.0 (s), 45.9 (s), 47.8 (d), 49.3 (d), 72.4 (d), 114.3 (s), 114.7 (s), 123.5 (s), 123.7 (d), 165.2 (d), 169.4 (s), 196.3 (s), 197.6 (s) ppm 7) high-performance liquid chromatography:
column: Unison UK-C18
(4.6 mm in diameter×75 mm in length; manufactured by Imtakt Corp.)
Solvent:
A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
temperature: 40° C.
detection: ultraviolet absorption λ230 nm
retention time: 3.7 minutes,

(15) a method for producing a compound according to any one of (1), (2), (7), and (8), comprising using a compound represented by the following formula (VIII):

[Formula 8]

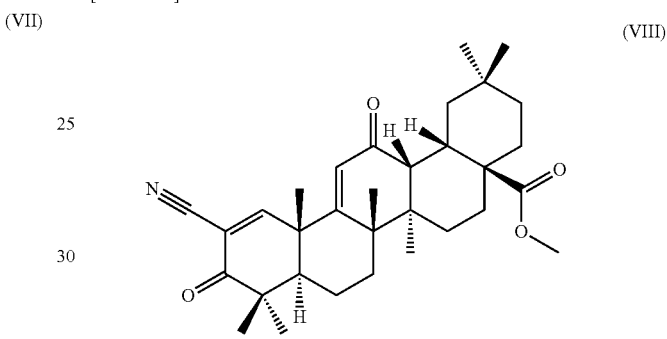

(VIII)

as a substrate, culturing this compound in a medium together with a strain for biotransformation of the genus *Cunninghamella* capable of transforming the compound to the compound according to any one of (1), (2), (7), and (8), and collecting the compound according to any one of (1), (2), (7), and (8) from the culture,

(16) the method for producing a compound according to (15), wherein the strain for biotransformation is *Cunninghamella elegans* SANK 10412 strain (Deposition No. NITE BP-1487) belonging to the genus *Cunninghamella*,

(17) a method for producing a compound according to any one of (3) to (6), comprising using a compound represented by the following formula (VIII):

[Formula 9]

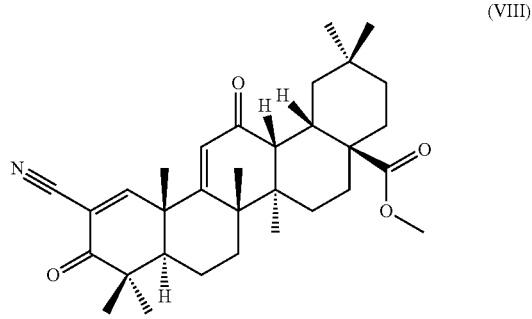

(VIII)

as a substrate, culturing this compound in a medium together with a strain for biotransformation of the genus *Chaetomium* capable of transforming the compound to the compound according to any one of (3) to (6), and collecting the compound according to any one of (3) to (6) from the culture,

(18) the method for producing a compound according to (17), wherein the strain for biotransformation is *Chaetomium globosum* SANK 10312 (Deposition No. NITE BP-1486) belonging to the genus *Chaetomium*,

(19) a method for producing a compound according to any one of (3) to (6), comprising using a compound represented by the following formula (VIII):

[Formula 10]

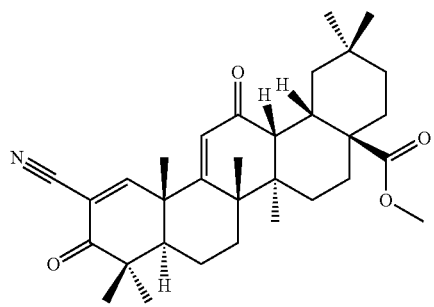

(VIII)

as a substrate, culturing this compound in a medium together with a strain for biotransformation of the genus *Mucor* capable of transforming the compound to the compound according to any one of (3) to (6), and collecting the compound according to any one of (3) to (6) from the culture,

(20) the method for producing a compound according to (19), wherein the strain for biotransformation is *Mucor hiemalis* f. *hiemalis* SANK 10612 (Deposition No. NITE BP-1488) belonging to the genus *Mucor*,

(21) a method for producing a compound according to (9) or (10), comprising using a compound represented by the following formula (IX):

[Formula 11]

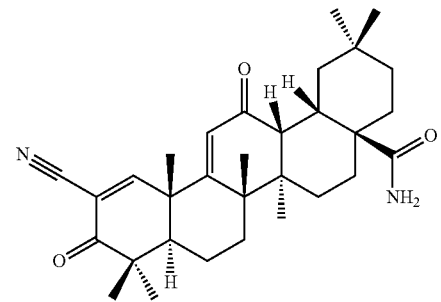

(IX)

as a substrate, culturing this compound in a medium together with a strain for biotransformation of the genus *Chaetomium* capable of transforming the compound to the compound according to (9) or (10), and collecting the compound according to (9) or (10) from the culture,

(22) a method for producing a compound according to any one of (11) to (14), comprising using a compound represented by the following formula (X):

[Formula 12]

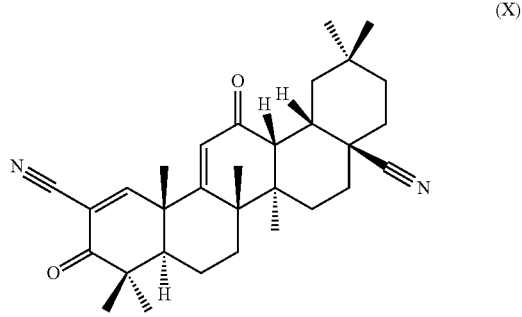

(X)

as a substrate, culturing this compound in a medium together with a strain for biotransformation of the genus *Chaetomium* capable of transforming the compound to the compound according to any one of (11) to (14), and collecting the compound according to any one of (11) to (14) from the culture,

(23) *Cunninghamella elegans* SANK 10412 (Deposition No. NITE BP-1487) belonging to the genus *Cunninghamella*,

(24) *Chaetomium globosum* SANK 10312 (Deposition No. NITE BP-1486) belonging to the genus *Chaetomium*,

(25) *Mucor hiemalis* f. *hiemalis* SANK 10612 (Deposition No. NITE BP-1488) belonging to the genus *Mucor*,

(26) a medicament comprising a terpenoid derivative according to any one of (1) to (14) as an active ingredient,

(27) a preventive or therapeutic agent for an eye disease (the eye disease is allergic conjunctival disease, viral conjunctivitis, pterygium, corneal infection, dry eye, corneal disorder (which is corneal epithelial disorder and/or corneal endothelial disorder), uveitis, Behcet's disease, diabetic retinopathy, retinal detachment, retinal vein occlusion, central serous chorioretinopathy, age-related macular degeneration, diabetic macular edema, macular disease, retinitis pigmentosa, glaucoma, or cataract), a renal disease (the renal disease is acute nephritis, chronic nephritis, acute renal failure, chronic renal failure, nephrotic syndrome, IgA nephropathy, diabetic nephropathy, gouty kidney, nephrosclerosis, hydronephrosis, tubulointerstitial nephritis, decreased renal function after coronary-artery bypass surgery, or urinary tract infection), a respiratory disease (the respiratory disease is bronchitis, pneumonia, pleuritis, chronic obstructive pulmonary disease, acute lung injury (ALI), diffuse panbronchiolitis, pulmonary emphysema, or asthma), a hepatic disease (the hepatic disease is alcoholic fatty liver, non-alcoholic steatohepatitis, hepatic fibrosis, liver cirrhosis, or hepatic dysfunction associated with liver transplantation), a brain disease (the brain disease is Alzheimer's disease, Parkinson's disease, Huntington's disease, amyotrophic lateral sclerosis (ALS), cerebral infarction, or multiple sclerosis), or a heart disease (the heart disease is myocardial infarction), comprising a terpenoid derivative according to any one of (1) to (14) as an active ingredient,

(28) a preventive or therapeutic agent for an eye disease (the eye disease is dry eye, corneal disorder (which is corneal epithelial disorder and/or corneal endothelial disorder), uveitis, diabetic retinopathy, retinal vein occlusion, age-related macular degeneration, diabetic macular edema, or glaucoma), a renal disease (the renal disease is diabetic nephropathy), a respiratory disease (the respiratory disease is chronic obstructive pulmonary disease or acute lung injury), a hepatic disease (the hepatic disease is non-alcoholic steatohepatitis, liver cirrhosis, or hepatic dysfunction associated with liver transplantation), or a brain disease (the brain disease is cerebral infarction or multiple sclerosis)

comprising a terpenoid derivative according to any one of (1) to (14) as an active ingredient,

(29) a preventive or therapeutic agent for dry eye, comprising a terpenoid derivative according to any one of (1) to (14) as an active ingredient,

(30) a preventive or therapeutic agent for a disorder of the corneal epithelium and/or the corneal endothelium, comprising a terpenoid derivative according to any one of (1) to (14) as an active ingredient,

(31) a preventive or therapeutic agent for age-related macular degeneration, comprising a terpenoid derivative according to any one of (1) to (14) as an active ingredient,

(32) a preventive or therapeutic agent for diabetic macular edema and/or retinal vein occlusion, comprising a terpenoid derivative according to any one of (1) to (14) as an active ingredient,

(33) a preventive or therapeutic agent for chronic obstructive pulmonary disease, comprising a terpenoid derivative according to any one of (1) to (14) as an active ingredient,

(34) a preventive or therapeutic agent for cerebral infarction, comprising a terpenoid derivative according to any one of (1) to (14) as an active ingredient, and

(35) a preventive or therapeutic agent for multiple sclerosis, comprising a terpenoid derivative according to any one of (1) to (14) as an active ingredient.

The terpenoid derivative represented by the chemical structural formula according to (1) or the terpenoid derivative having the physicochemical properties according to (2) is referred to as terpenoid derivative A.

The terpenoid derivative represented by the chemical structural formula according to (3) or the terpenoid derivative having the physicochemical properties according to (4) is referred to as terpenoid derivative B.

The terpenoid derivative represented by the chemical structural formula according to (5) or the terpenoid derivative having the physicochemical properties according to (6) is referred to as terpenoid derivative C.

The terpenoid derivative represented by the chemical structural formula according to (7) or the terpenoid derivative having the physicochemical properties according to (8) is referred to as terpenoid derivative D.

The terpenoid derivative represented by the chemical structural formula according to (9) or the terpenoid derivative having the physicochemical properties according to (10) is referred to as terpenoid derivative E.

The terpenoid derivative represented by the chemical structural formula according to (11) or the terpenoid derivative having the physicochemical properties according to (12) is referred to as terpenoid derivative F.

The terpenoid derivative represented by the chemical structural formula according to (13) or the terpenoid derivative having the physicochemical properties according to (14) is referred to as terpenoid derivative G.

The terpenoid derivatives A to G are also collectively referred to as the terpenoid derivative of the present invention.

The terpenoid derivative of the present invention may form a solvate. Also, the terpenoid derivative of the present invention, when left in air, may have adsorbed water or form a hydrate by absorbing moisture. Such a solvate or hydrate is also included in the present invention.

The terpenoid derivative of the present invention may have geometric isomers (cis and trans isomers) and optical isomers based on an asymmetric center in the molecule or the like. The present invention also encompasses all of these isomers and mixtures of these isomers at arbitrary ratios.

Advantageous Effects of Invention

The terpenoid derivative of the present invention is excellent in anti-inflammatory action and cytoprotective action and is useful as a therapeutic drug for an eye disease, a renal disease, a respiratory disease, a hepatic disease, diabetes mellitus and its complications, or the like.

DESCRIPTION OF EMBODIMENTS

Figure 1:
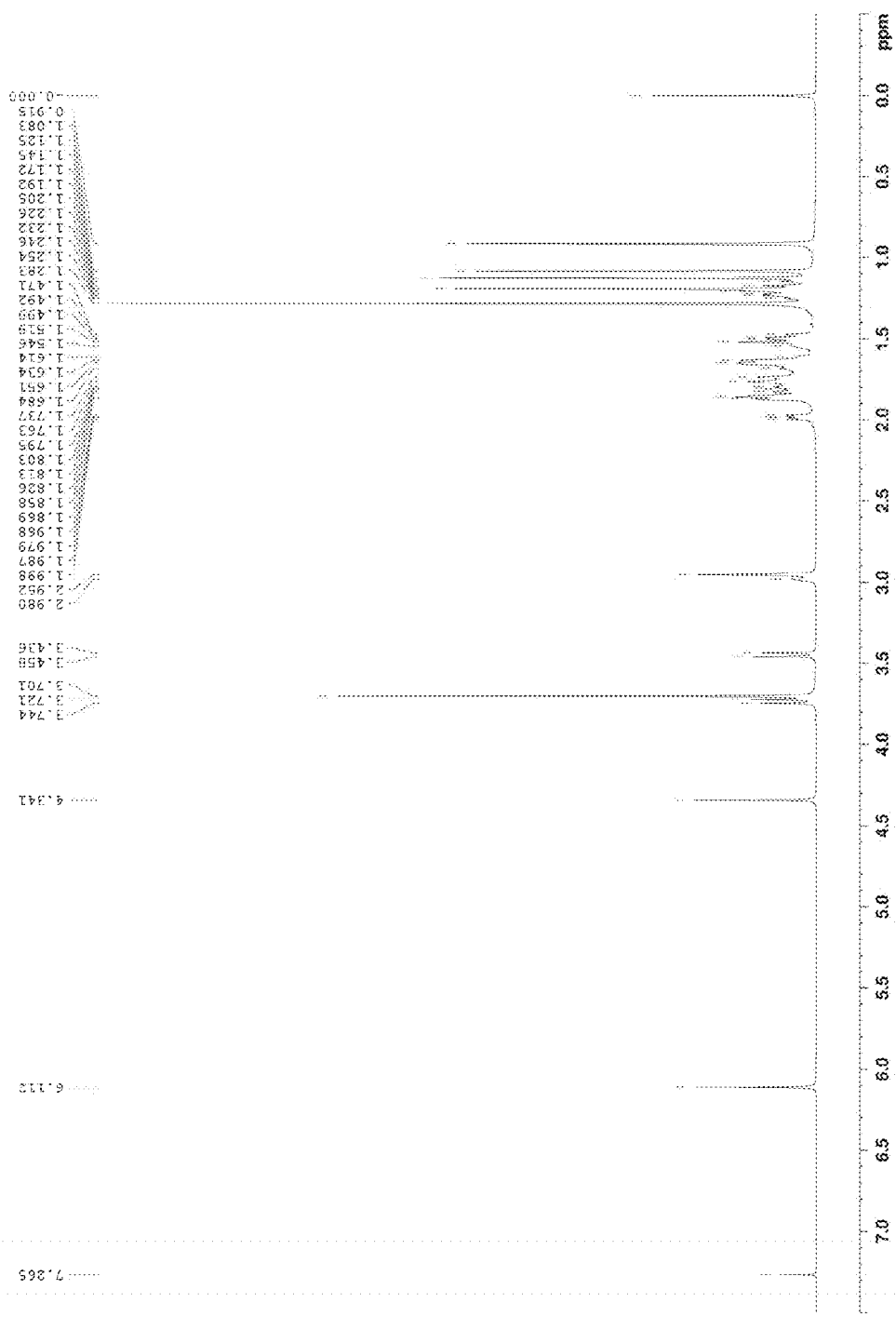
FIG. 1 shows the 1H-NMR spectra of terpenoid derivative A.

The terpenoid derivative of the present invention can be isolated and purified according to a routine methods from cultures of a microbe having the ability to transform a specific substrate compound to the terpenoid derivative of the present invention [in the present invention, referred to as a strain for biotransformation].

1. Substrate Compound

A compound represented by the following formula (VIII) can be used as a substrate for the production of the terpenoid derivative of the present invention.

[Formula 13]

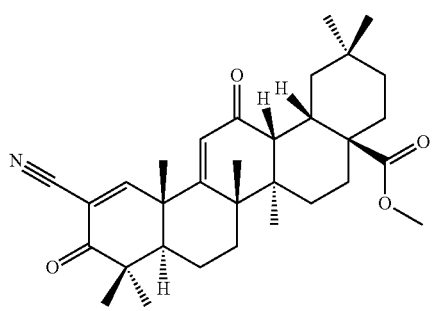

(VIII)

The compound is referred to bardoxolone methyl by its generic name. The compound is described as compound No. 17 in Synthesis Scheme 2 in Bioorganic & Medicinal Chemistry Letters 8 (1998) 2711-2714 and is also referred to as methyl 2-cyano-3,12-dioxooleana-1,9-dien-28-oate (CDDO-Me). Hereinafter, the substrate compound is also referred to as CDDO-Me.

CDDO-Me can be produced according to a synthesis method described in Bioorganic & Medicinal Chemistry Letters 7 (1997) 1623-1628 and Bioorganic & Medicinal Chemistry Letters 8 (1998) 2711-2714.

Alternatively, a compound represented by the following formula (IX) can be used as a substrate for the production of the terpenoid derivative of the present invention.

[Formula 14]

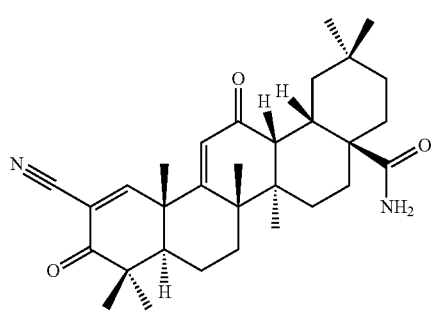

(IX)

The compound is described as compound No. 15 in Synthesis Scheme 1 in Bioorganic & Medicinal Chemistry Letters 12 (2002) 1027-1030. The compound can be produced according to a synthesis method described in Bioorganic & Medicinal Chemistry Letters 12 (2002) 1027-1030.

Alternatively, a compound represented by the following formula (X) can be used as a substrate for the production of the terpenoid derivative of the present invention.

[Formula 15]

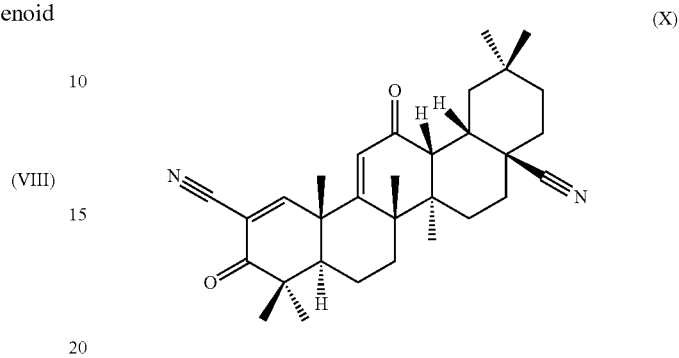

(X)

The compound is described as compound No. 4 in Synthesis Scheme 1 in Bioorganic & Medicinal Chemistry Letters 12 (2002) 1027-1030. The compound can be produced according to a synthesis method described in Bioorganic & Medicinal Chemistry Letters 12 (2002) 1027-1030.

2. Production from Substrate Compound (1) Strain for Biotransformation

The strain for biotransformation used for the production of terpenoid derivative A or terpenoid derivative D of the present invention from the substrate compound is not particularly limited and is preferably a fungus. Examples thereof include a fungus belonging to the genus *Cunninghamella*.

The fungus belonging to the genus *Cunninghamella* is preferably *Cunninghamella elegans*, more preferably *Cunninghamella elegans* SANK 10412 (Deposition No. NITE BP-1487) (hereinafter, referred to as "SANK 10412").

SANK 10412 was separated from the soil of Chiba prefecture in April 1993.

The strain for biotransformation used for the production of terpenoid derivative B, terpenoid derivative C, terpenoid derivative E, terpenoid derivative F, or terpenoid derivative G of the present invention from the substrate compound is not particularly limited and is preferably a fungus. Examples thereof include a fungus belonging to the genus *Chaetomium* or *Mucor*.

The fungus belonging to the genus *Chaetomium* is preferably *Chaetomium globosum*, more preferably *Chaetomium globosum* SANK 10312 (Deposition No. NITE BP-1486) (hereinafter, referred to as "SANK 10312").

SANK 10312 was separated from the fresh water of Kyoto prefecture in November 2000.

The fungus belonging to the genus *Mucor* is preferably *Mucor hiemalis* f. *hiemalis*, more preferably a *Mucor hiemalis* f. *hiemalis* SANK 10612 strain (Deposition No. NITE BP-1488) (hereinafter, referred to as "SANK 10612").

SANK 10612 was separated from a sample collected in Ibaraki prefecture in August 1999.

In order to identify the fungal strains SANK 10312, SANK 10412, and SANK 10612, the following 5 types of media were used in fungal culture, and their compositions were as follows:

<PDA Medium (Potato Dextrose Agar Medium)>
Nissui potato dextrose agar medium (manufactured by

| Nissui Pharmaceutical Co., Ltd.) | 39 g |
| Distilled water | 1000 ml |

<MEA (CBS) medium {malt extract agar (CBS) medium}>
Bacto Malt Extract (manufactured by Becton, Dickinson and

| Bacto Malt Extract (manufactured by Becton, Dickinson and Company) | 20 g |
| Agar | 15 g |
| Distilled water | 1000 ml |

<OA medium (oatmeal agar medium)>

| Oatmeal extract* | 1000 ml |
| Agar | 20 g |

*To 30 g of oatmeal, distilled water was added, and the mixture was decocted for insomuch as 2 hours and filtered through cloth, followed by fill-up to 1000 ml to prepare the oatmeal extract.

<MEA medium (malt extract agar medium)>

| Bacto Malt Extract (manufactured by Becton, Dickinson and Company) | 30 g |
| Bacto Soytone (manufactured by Becton, Dickinson and Company) | 3 g |
| Agar | 15 g |
| Distilled water | 1000 ml |

<CMA medium (corn meal agar medium)>

| Corn meal agar "Nissui" (manufactured by Nissui Pharmaceutical Co., Ltd.) | 17 g |
| Distilled water | 1000 ml |

In the description below, the color is indicated according to Kornerup, A. & Wanscher, J. H. 1978. Methuen handbook of colour (3rd. edition). Erye Methuen, London.

The mycological properties of SANK 10312 are as given below.

SANK 10312 was inoculated to 4 types of media (PDA medium, OA medium, CMA medium, and MEA medium), and its mycological properties were observed.

The growth temperature of SANK 10312 in the PDA medium was 9 to 33° C., and this strain grew well, particularly, at 18 to 31° C.

The mycological properties of SANK 10312 are as follows:

The colonies in the OA medium are 80 mm or larger in diameter by culture at 28° C. for 10 days. The colonies are thin and composed of white and short cottony hyphae, and are grayish-yellow with grayish brown to yellowish brown concentrically at a site slightly distant from the center. The central portion of the colony densely forms small granular ascomata on the surface and is dark green. The reverse side is pale yellow to brownish orange with an olive brown color at the central portion and a dark brown color concentrically at a site slightly distant from the center.

The colonies in the MEA medium are 80 mm or larger in diameter by culture at 28° C. for 10 days. The colonies are thin and composed of white and short cottony hyphae, and are brownish orange. Neither conidia nor ascomata are formed. The reverse side is similar thereto.

The colonies in the CMA medium are 60 mm in diameter by culture at 28° C. for 10 days. The colonies are very thin and merely have sparse hyphae on the surface of the agar. The surface color of the colony is almost colorless and clear, and the reverse side is similar thereto.

The growth temperature of SANK 10312 in the PDA medium is 9 to 33° C., and this strain grows well, particularly, at 18 to 31° C.

The microscopic structure of SANK 10312 in the OA medium at day 10 at 28° C. is as follows:

The ascomata are dark brown to black, have subspherical to oval shape of 175 to 240 µm in width and 275 to 400 µm in height, and have peridium composed of *textura intricata* and ostiole at the apex. The lateral hairs are straight or slightly wavy, pale olive, and 3.5 µm or smaller in diameter, and are integrated with terminal hairs in the upper region of the ascomata. A large number of terminal hairs are dense and wavy or loosely coiled toward the tip and have rough surface as a whole, have septa, and a round tip. The terminal hairs are 3 to 4 µm in basal width and olive and become thinner and lighter toward the tip. The asci are club-shaped and octosporous. The ascospores are lemon-shaped and are light brown when immature and pale green to dark olive brown and 6.0 to 9.0×8.0 to 11.0 µm when mature. No conidia are observed.

The mycological features as mentioned above are well consistent with the description about *Chaetomium globosum* Kunze in Compendium of Soil Fungi (DOMSCH, K. H., W. GAMS and T.-H. ANDERSON (2007) Compendium of Soil Fungi. 2nd ed. revised by W. Gams. 2007.382 FIGS. 672 p). Thus, this fungal strain was identified as *Chaetomium globosum* and designated as *Chaetomium globosum* SANK 10312.

SANK 10312 was internationally deposited under Deposition No. NITE BP-1486 with NITE Patent Microorganisms Depositary (NPMD), Biological Resource Center, National Institute of Technology and Evaluation (address: 2-5-8 Kazusakamatari, Kisarazu-shi, Chiba, Japan) on Dec. 18, 2012.

The mycological properties of SANK 10412 are as given below.

SANK 10412 was inoculated to 2 types of media (PDA medium and MEA (CBS) medium), and its mycological properties were observed.

The growth temperature of SANK 10412 in the PDA medium was 8 to 35° C., and this strain grew well, particularly, at 25 to 35° C.

The mycological properties of SANK 10412 are as follows:

The colonies in the PDA medium are 7.0 cm in diameter by culture at 23° C. for 4 days. The colonies are thin, and the hyphae are cottony, are slightly dense and rising at the central portion, are white, and develop sporangiophores and become dark gray when mature.

The colonies in the MEA (CBS) medium are 6.0 to 6.5 cm in diameter by culture at 23° C. for 4 days. The colonies are thin, and the hyphae are cottony, are white color, and develop sporangiophores and become dark gray when mature.

The microscopic structure of SANK 10412 in the MEA (CBS) medium at day 4 at 23° C. are as follows:

The sporangiophores are 6 to 13.5 µm in diameter, are verticillate or branched, and form vesicles at their respective tips. The vesicles are subspherical to piriform in shape and 13 to 35 μm in width, develop a large number of pedicels on the surface, and each form one sporangiospore at the tip. The sporangiospores are almost colorless each alone and are dark gray to black when gathered. The sporangiospores are unicellular and spherical to ellipsoidal in shape, have smooth surface or short spikes, and have a diameter of 5.0 to 9.0 μm. No zygospore was observed.

The mycological features as mentioned above are well consistent with the description about *Cunninghamella elegans* Lendn. in p. 164-165 of Compendium of Soil Fungi (idem). Thus, this fungal strain was identified as *Cunninghamella elegans* and designated as *Cunninghamella elegans* SANK 10412.

SANK 10412 was internationally deposited under Deposition No. NITE BP-1487 with NITE Patent Microorganisms Depositary (NPMD), Biological Resource Center, National Institute of Technology and Evaluation (address: 2-5-8 Kazusakamatari, Kisarazu-shi, Chiba, Japan) on Dec. 18, 2012.

The mycological properties of SANK 10612 are as given below.

SANK 10612 was inoculated to 2 types of media (PDA medium and MEA (CBS) medium), and its mycological properties were observed.

The growth temperature of SANK 10612 in the PDA medium was 10 to 31° C., and this strain grew well, particularly, at 19 to 27° C.

The colonies in the PDA medium are 7.5 to 8.0 cm in diameter by culture at 20° C. for 4 days. The colonies are slightly dense and rising at the central portion, and the hyphae are cottony, brown to brownish gray, and are white at the marginal portion. The reverse side has similar colors. Sporangiospores are formed.

The colonies in the MEA (CBS) medium are 6 to 6.5 cm in diameter by culture at 20° C. for 4 days. The colonies are thin, and the hyphae are cottony and white. Sporangiospores are sparsely formed.

The microscopic structure of SANK 10612 in MEA (CBS) at day 4 at 20° C. is as follows:

The sporangiophores are 16 μm or smaller in diameter, are sympodially branched infrequently, and form sporangia at their tips. The sporangia are initially yellow and become dark brown when mature. The sporangia are 70 μm or smaller in diameter and have soluble walls. The columellae are spherical to ellipsoidal in shape, have collars, and have a width of 13.5 to 29.5 μm and a diameter of 15 to 32 μm. The sporangiospores are colorless and are unicellular, smooth, and ellipsoidal to nephroid in shape, and their sizes largely vary and are 3.0 to 9.5×2 to 5 μm. Neither chlamydospore nor zygospore was observed.

The mycological features as mentioned above are well consistent with the description about *Mucor hiemalis* f. *hiemalis* Wehmer in p. 293-294 of Compendium of Soil Fungi (idem). Thus, this fungal strain was identified as *Mucor hiemalis* f. *hiemalis* and designated as *Mucor hiemalis* f. *hiemalis* SANK 10612.

SANK 10612 was internationally deposited under Deposition No. NITE BP-1488 with NITE Patent Microorganisms Depositary (NPMD), Biological Resource Center, National Institute of Technology and Evaluation (address: 2-5-8 Kazusakamatari, Kisarazu-shi, Chiba, Japan) on Dec. 18, 2012.

As is well known, fungi are susceptible to mutation in the natural world or by artificial operation (e.g., ultraviolet irradiation, radiation, or chemical agent treatment). Presumably, SANK 10312, SANK 10412, and SANK 10612 of the present invention are also susceptible to such mutation.

In the present invention, SANK 10312, SANK 10412, and SANK 10612 encompass all of their variants.

These variants also encompass those obtained by a genetic method, for example, recombination, transduction, or biotransformation.

Specifically, SANK 10312, SANK 10412, and SANK 10612 as the strain for biotransformation used for the production of the terpenoid derivative of the present invention, their variants, and fungal strains that are not clearly distinguished therefrom are all included in SANK 10312, SANK 10412, and SANK 10612.

(2) Culture method and purification method (production and purification of terpenoid derivative of the present invention)

The aforementioned strain for biotransformation can be cultured using a medium as generally used in the production of secondary metabolites of microbes. Such a medium contains a carbon source, a nitrogen source, an inorganic salt, a very small amount of a growth factor, a trace metal, and the like, utilizable by microbes Examples of the carbon source include glucose, fructose, maltose, sucrose, mannitol, glycerin, dextrin, oat, rye, starch, potato, corn flour, cottonseed oil, molasses, citric acid, and tartaric acid. These carbon sources can be used alone or in combination.

The amount of the carbon source added is usually in the range of 1 to 10% by weight of the amount of the medium.

A substance containing a protein and a hydrolysate thereof, or an inorganic salt is usually used as the nitrogen source.

Examples of such a nitrogen source include soybean flour, bran, peanut flour, cottonseed meal, casein hydrolysates, Pharmamin, fish meal, corn steep liquor, peptone, meat extracts, yeast, yeast extracts, malt extracts, sodium nitrate, ammonium nitrate, and ammonium sulfate. These nitrogen sources can be used alone or in combination.

The amount of the nitrogen source added is usually in the range of 0.2 to 10% by weight of the amount of the medium.

Also, salts capable of providing ions of sodium, potassium, magnesium, ammonium, calcium, phosphate, sulfate, chloride, carbonate, or the like may be added into the medium.

Vitamins such as vitamin B1 and biotin, a substance promoting fungus body proliferation, such as thiamin, and a salt of a metal such as manganese or molybdenum, utilizable by microbes may be further added into the medium.

In the case of a liquid medium, an antifoaming agent such as silicon oil, a polyalkylene glycol ether, a plant oil, an animal oil, or a surfactant may be added to the medium in order to prevent the foaming of the medium.

The pH of the liquid medium for use in the culture of the strain for biotransformation depends on the pH stability of the fungal strain and the terpenoid derivative of the present invention, etc.

The culture temperature of the strain for biotransformation depends on the thermal stability of the fungal strain and the terpenoid derivative of the present invention, etc. In the case where the strain for biotransformation is SANK 10312 strain, the culture temperature is preferably 9 to 33° C., more preferably 20 to 35° C. In the case where the strain for biotransformation is SANK 10412 strain, the culture temperature is preferably 8 to 35° C., more preferably 20 to 35° C. In the case where the strain for biotransformation is SANK 10612 strain, the culture temperature is preferably 10 to 31° C., more preferably 20 to 27° C.

Examples of the method for culturing the strain for biotransformation can include, but are not particularly limited to, a culture method using a solid medium, a stirring culture method, a shake culture method, an aeration culture method, and an aeration stirring culture method. The culture method is preferably a stirring culture method, a shake culture method, an aeration culture method, and an aeration stirring culture method, more preferably a shake culture method. The aeration stirring culture method is more preferred for culture at an industrial scale.

The culture of the strain for biotransformation usually starts from seed culture using a small amount of a medium inoculated with a slant having the strain for biotransformation and is achieved by optional seed culture carried out again at a larger scale followed by main culture at a larger scale at the final stage.

In the case of culturing the strain for biotransformation at a small scale, seed culture is carried out using an Erlenmeyer flask or the like, and, if necessary, seed culture is carried out again at a larger scale, followed by main culture using an Erlenmeyer flask or the like.

In the case of culturing the strain for biotransformation at a large scale, a jar fermenter or a tank equipped with a stirring apparatus and an aeration apparatus is preferably used. Use of such an apparatus allows the medium to be prepared and sterilized in the jar fermenter or the tank. This method is suitable for large-scale production.

As for the culture time, culture for 120 to 192 hours after addition of the substrate usually reaches the maximum level.

After the completion of the culture, the terpenoid derivative of the present invention can be extracted from the obtained culture, the fungus body contained therein, and/or the culture supernatant. A centrifugation method or a filtration method with diatomaceous earth as a filter aid can be used for separating the fungus body and other solid materials from the culture supernatant.

For the extraction of the terpenoid derivative of the present invention, the physicochemical properties of the compound can be utilized. The terpenoid derivative of the present invention contained in the culture filtrate or the culture supernatant can be extracted with a water-immiscible organic solvent such as ethyl acetate, chloroform, ethylene chloride, methylene chloride, or butanol, or a mixed solvent of two or more of these solvents. The terpenoid derivative of the present invention contained in the fungus body can be extracted therefrom using 50 to 90% aqueous acetone or aqueous methanol and extracted in the same way as in the case where the terpenoid derivative is present in the culture filtrate or the culture supernatant, after distilling off of the organic solvent. The terpenoid derivative of the present invention contained in the whole cultures can be extracted by the addition of 20 to 80%, preferably 40 to 60%, more preferably 50%, of acetone or methanol to the whole culture. After completion of the extraction, the extracts are filtered with diatomaceous earth as a filter aid, and the terpenoid derivative can be extracted from the obtained soluble matter in the same way as in the case where the terpenoid derivative is present in the culture filtrate or the culture supernatant.

The purification for isolating the terpenoid derivative of the present invention from the extracts can be carried out by a purification technique such as adsorption chromatography, ion-exchange chromatography, partition chromatography, reverse-phase chromatography, or high-performance liquid chromatography (hereinafter, referred to as HPLC).

The adsorption chromatography is carried out by: contacting the extracts containing the terpenoid derivative of the present invention with an adsorbent to remove impurities through adsorption; or adsorbing the terpenoid derivative of the present invention to remove impurities, followed by elution. Examples of the adsorbent can include active carbon, Amberlite XAD-2, Amberlite XAD-4, and Amberlite XAD-16 (all manufactured by Rohm and Haas Company), and Diaion HP-20, Diaion HP-21, Diaion HP-20SS, Sepabeads SP-207, Sepabeads SP-850, and Sepabeads SP-700 (all manufactured by Mitsubishi Chemical Corp.). Examples of the solvent for use in the elution of the adsorbed terpenoid derivative of the present invention can include organic solvents such as methanol, acetone, butanol, and acetonitrile, and mixed solutions thereof with water.

The ion-exchange chromatography is carried out by use of the fact that the terpenoid derivative of the present invention behaves as a neutral substance. Specifically, the extracts containing the terpenoid derivative of the present invention are contacted with, for example, an ion-exchange carrier to adsorb unnecessary matter onto the carrier while passing the terpenoid derivative of the present invention therethrough. Examples of the ion-exchange carrier can include DEAE-Sephadex, DEAE-Sepharose, QAE-Sephadex, CM-Sephadex, and SP-Sephadex (all manufactured by GE Healthcare Life Sciences), DEAE-Toyopearl, QAE-Toyopearl, CM-Toyopearl, and SP-Toyopearl (all manufactured by Tosoh Corp.), Duolite A113LF, Duolite A116, Duolite A368S, Duolite A375LF, Duolite C20J, and Duolite C433LF (all manufactured by Diamond Shamrock Chemical Company), Amberlite IRA-67, Amberlite IRA-98, Amberlite IRA400J, Amberlite IRA458RF, Amberlite IR120B, and Amberlite IRC76 (all manufactured by Rohm and Haas Company), and Dowex 50WX4, Dowex HCR-S, Dowex 1×4, Dowex 22, Dowex 66, and Dowex SBR-P (manufactured by The Dow Chemical Company).

Examples of the carrier for use in the partition chromatography can include silica gel, TSK gel Toyopearl HW-40F (manufactured by Tosoh Corp.), Sephadex LH-20 (manufactured by GE Healthcare Life Sciences), and cellulose (manufactured by Merck KGaA).

Examples of the carrier for use in the reverse-phase chromatography can include Cosmosil 140C18 (manufactured by Nacalai Tesque, Inc.) and ODS-A (manufactured by YMC Co., Ltd.).

Examples of the column for use in the HPLC can include reverse-phase columns such as Shodex Asahipak ODP50-4E (manufactured by Showa Denko K.K.), YMC pack ODS-A (manufactured by YMC Co., Ltd.), CAPCELL PAK UG120 (manufactured by Shiseido Co., Ltd.), and Unison C18 (manufactured by Imtakt Corp.).

The terpenoid derivative of the present invention can be isolated using these purification techniques alone or in appropriate combination. If necessary, the same purification technique may be repeated. A method suitable for purification, such as a column chromatography method, a batch chromatography method, a thin-layer chromatography method, can be selected in order to carry out each purification technique.

The steric structure of the obtained terpenoid derivative of the present invention is derived from the steric structure of the starting compound. The steric structures of substituents newly introduced to the starting compound were determined using two-dimensional nuclear magnetic resonance spectroscopy (NOESY).

For example, the planar structural formula of terpenoid derivative A having the physicochemical properties described in (2) above is as represented by the formula (I') given below. The steric structure of terpenoid derivative A was determined to be a steric structure represented by the formula (I) from the steric structure of the starting compound, the physicochemical properties described in (2), and measurement results of two-dimensional nuclear magnetic resonance spectroscopy (NOESY) described later in Example 3.

Likewise, the planar structural formula of terpenoid derivative B having the physicochemical properties described in (4) above is as represented by the formula (II') given below. The planar structural formula of terpenoid derivative C having the physicochemical properties described in (6) above is as represented by the formula (III') given below. The steric structures of terpenoid derivative B and terpenoid derivative C were determined to be steric structures represented by the formula (II) and the formula (III), respectively, from the steric structure of the starting compound, the physicochemical properties described in (4), the physicochemical properties described in (6), and measurement results of two-dimensional nuclear magnetic resonance spectroscopy (NOESY) described later in Example 1.

[Formula 16]

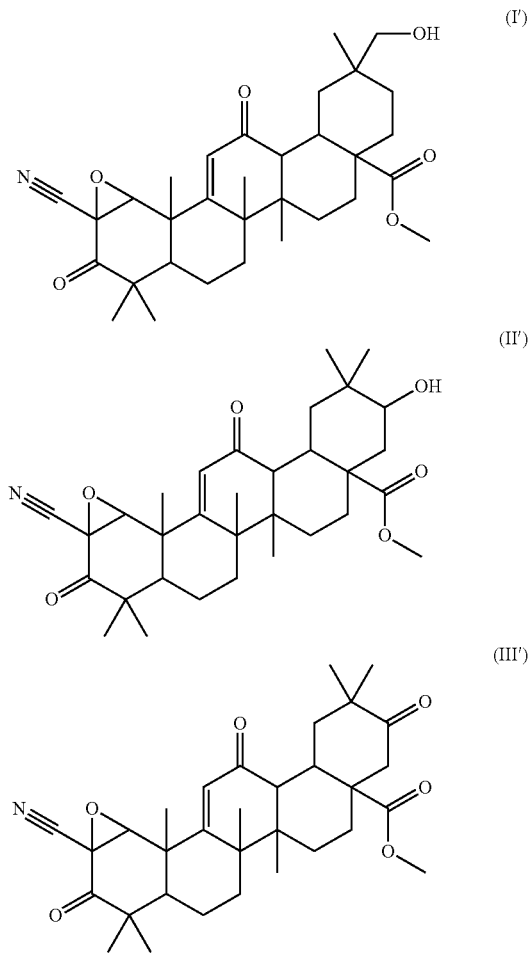

3. Medicament Comprising Terpenoid Derivative of the Present Invention

The terpenoid derivative of the present invention purified as mentioned above has the action of activating the Keap1/Nrf2/ARE signaling pathway and has an anti-inflammatory action and a cytoprotective action.

Activation of the Keap1/Nrf2/ARE signaling pathway induces its target gene of NAD(P)H:quinone oxidoreductase-1 (NQO1), heme oxygenase-1 (HO-1), γ-glutamate cysteine ligase catalytic subunit (GCLC), or the like (Non-patent Literature 1). When these enzymes are increased in amount or activated, the cells become resistant to poison, oxidative stress, inflammation, etc. The terpenoid derivative of the present invention is therefore useful as a preventive or therapeutic agent for diseases such as an eye disease, a renal disease, a hepatic disease, and diabetes mellitus and its complications.

Examples of the eye disease include diseases such as allergic conjunctival disease, viral conjunctivitis, pterygium, corneal infection, dry eye, corneal disorder (which is corneal epithelial disorder and/or corneal endothelial disorder), uveitis, Behcet's disease, diabetic retinopathy, retinal detachment, retinal vein occlusion (RVO), central serous chorioretinopathy, age-related macular degeneration (AMD), diabetic macular edema (DME), macular disease, retinitis pigmentosa, glaucoma, and cataract.

Examples of the renal disease include diseases caused by kidney problems, such as acute nephritis, chronic nephritis, acute renal failure, chronic renal failure, nephrotic syndrome, IgA nephropathy, diabetic nephropathy, gouty kidney, nephrosclerosis, hydronephrosis, tubulointerstitial nephritis, decreased renal function after coronary-artery bypass surgery, and urinary tract infection.

Examples of the respiratory disease include bronchitis, pneumonia, pleuritis, chronic obstructive pulmonary disease (COPD), acute lung injury (ALI), diffuse panbronchiolitis, pulmonary emphysema, and asthma.

Examples of the hepatic disease include alcoholic fatty liver, non-alcoholic steatohepatitis, hepatic fibrosis, liver cirrhosis, and hepatic dysfunction associated with liver transplantation.

Examples of the brain disease include Alzheimer's disease, Parkinson's disease, Huntington's disease, amyotrophic lateral sclerosis (ALS), cerebral infarction, and multiple sclerosis (MS).

Examples of the heart disease include myocardial infarction.

Examples of diabetes mellitus and its complications include diabetic retinopathy, diabetic nephropathy, and diabetic neuropathy.

The terpenoid derivative of the present invention is particularly useful as a preventive or therapeutic agent for, among these diseases, dry eye, corneal disorder (which is corneal epithelial disorder and/or corneal endothelial disorder), uveitis, diabetic retinopathy, retinal vein occlusion, age-related macular degeneration, diabetic macular edema, or glaucoma as the eye disease, diabetic nephropathy as the renal disease, chronic obstructive pulmonary disease or acute lung injury (ALI) as the respiratory disease, non-alcoholic steatohepatitis or hepatic dysfunction associated with liver transplantation as the hepatic disease, or cerebral infarction or multiple sclerosis as the brain disease.

The terpenoid derivative of the present invention is further preferred as a preventive or therapeutic agent for dry eye, a preventive or therapeutic agent for a disorder of the corneal epithelium and/or the corneal endothelium, a preventive or therapeutic agent for age-related macular degeneration, a preventive or therapeutic agent for diabetic macular edema and/or retinal vein occlusion, a preventive or therapeutic agent for chronic obstructive pulmonary disease, a preventive or therapeutic agent for cerebral infarction, or a preventive or therapeutic agent for multiple sclerosis, among these diseases.

In the case of using the terpenoid derivative of the present invention as a medicament, this medicament can be administered in various forms. The dosage form depends on the preparation, age, sex, disease, etc. For example, tablets, pills, powders, granules, syrups, solutions, suspensions, emulsions, granules, or capsules are orally administered. For example, injections are administered intravenously, intramuscularly, intracutaneously, subcutaneously, intravitreally, intracamerally, subconjunctivally, to the capsule of Tenon, or intraperitoneally. Eye drops are instilled into the eyes. Eye ointments are used for ophthalmic mucous membranes. Suppositories are intrarectally administered. Any of these administration methods may be achieved by the administration of sustained-release preparations.

Various preparations containing the terpenoid derivative of the present invention as an active ingredient can be produced according to routine methods using known additives usually usable in the field of pharmaceutical preparations, such as excipients, binders, disintegrants, lubricants, solubilizers, corrigents, and coating agents.

For the formation of tablets, carriers known in the art can be widely used. Examples thereof can include: excipients such as lactose, saccharose, sodium chloride, glucose, urea, starch, calcium carbonate, kaolin, crystalline cellulose, and silicic acid; binders such as water, ethanol, propanol, simple syrup, dextrose in water, liquid starch, gelatin solution, carboxymethylcellulose, shellac, methylcellulose, potassium phosphate, and polyvinylpyrrolidone; disintegrants such as dry starch, sodium alginate, agar powder, laminaran powder, sodium bicarbonate, calcium carbonate, polyoxyethylene sorbitan fatty acid esters, sodium lauryl sulfate, monoglyceride stearate, starch, and lactose; disintegration inhibitors such as saccharose, stearin, cocoa butter, and hydrogenated oil; absorption promoters such as quaternary ammonium base and sodium lauryl sulfate; moisturizers such as glycerin and starch; adsorbents such as starch, lactose, kaolin, bentonite, and colloidal silicic acid; and lubricants such as purified talc, stearate, boric acid powder, and polyethylene glycol. The tablets can be prepared, if necessary, as tablets provided with usual coatings, for example, sugar-coated tablets, gelatin-coated tablets, enteric coated tablets, film-coated tablets, two-layered tablets, or multilayered tablets For the formation of pills, carriers known in the art can be widely used. Examples thereof can include: excipients such as glucose, lactose, starch, cocoa butter, hydrogenated plant oil, kaolin, and talc; binders such as gum arabic powder, gum tragacanth powder, gelatin, and ethanol; and disintegrants such as laminaran and agar.

In the case of preparations as injections, solutions and suspensions are preferably sterilized and isotonic to blood. For the formation of these solutions, emulsions, and suspensions, diluents known in the art can be widely used. Examples thereof can include water, ethyl alcohol, propylene glycol, epoxidized isostearyl alcohol, polyoxylated isostearyl alcohol, and polyoxyethylene sorbitan fatty acid esters. These preparations may contain common salt, glucose, or glycerin in an amount sufficient for maintaining tonicity. These preparations may contain dissolution aids, buffers, soothing agents, colorants, preservatives, fragrances, flavors, sweeteners, other agents, and the like.

In the case of intravenously administering an injection, the injection can be administered alone, as a mixture with a usual fluid replacement such as glucose or an amino acid, or as an emulsion with polyoxyethylene sorbitan fatty acid esters or the like.

For the formation of eye drops, solutions and suspensions are preferably sterilized and isotonic to blood. For the formation of these solutions, emulsions, and suspensions, diluents known in the art can be widely used. Examples of additives can include antiseptics, algefacients, and pH adjusters.

In the case of preparations as eye ointments, they are required, for example, to be sterile, to be free from mucosal irritation, not to be absorbed by the eyes, and to be well spreadable. Examples of bases include soft ophthalmic Vaseline. Liquid paraffin is used for dispersing the solid active ingredient as a find powder, and purified lanolin is used for the liquid active ingredient.

For the formation of suppositories, carriers known in the art can be widely used. Examples thereof can include polyethylene glycol, cocoa butter, higher alcohols, esters of higher alcohols, gelatin, and semisynthetic glyceride.

For the formulation of sustained-release preparations, agents known in the art can be widely used. Examples thereof can include biodegradable polymers such as polylactic acid, poly glycolic acid, and poly(lactic-co-glycolic acid). The sustained-release preparations include powder preparations intended for sustained release in the form of powders as well as dosage forms such as rods, sheets, films, discs, or microcapsules of the compound alone or sustained-release powders, and implant dosage forms using them.

The amount of the terpenoid derivative of the present invention contained in each of the pharmaceutical preparations mentioned above is not particularly limited and is preferably 1 to 80% by weight, more preferably 1 to 50% by weight.

The dose of the terpenoid derivative of the present invention differs depending on symptoms, age, etc., and is 0.0001 µg/site to 100 µg/site for local administration. The dose for systemic administration is 0.00001 mg/kg to 10 mg/kg.

The frequency of administration of the pharmaceutical preparation containing the terpenoid derivative of the present invention as an active ingredient is several times a day, once a day, or once every few days. The sustained-release preparation is administered once every two weeks, once every four weeks, once every three months, or once every six months as a guideline.

Next, the present invention will be described in more detail with reference to the Examples, Test Examples, and Formulation Examples. However, the present invention is not intended to be limited by these.

Example 1

Production of Terpenoid Derivative B and Terpenoid Derivative C

[Formula 17]

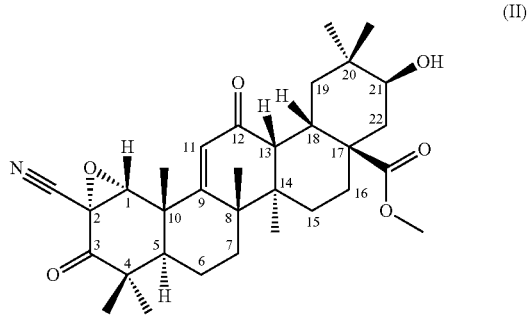

(II)

Terpenoid Derivative B

[Formula 18]

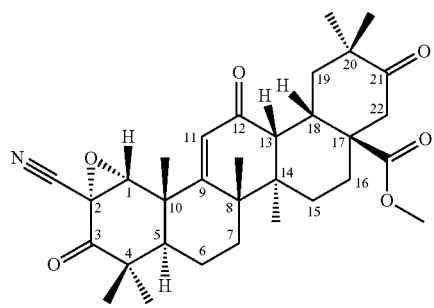

(III)

Terpenoid Derivative C (1) Culture of Strain for Biotransformation of Genus *Chaetomium*

20 ml of a seed culture medium having the composition shown in Table 1 below was placed in each of four 100-ml Erlenmeyer flasks, sterilized at 121° C. for 20 minutes, and then cooled to room temperature. 1 ml of a spore suspension of SANK 10312 was inoculated to the medium in each flask and cultured for 2 days under conditions of 23° C. and 210 rpm in a rotating shaker. Hereinafter, the obtained culture solution is referred to as a "seed culture solution".

TABLE 1

| Composition of seed culture medium for SANK 10312 | |
|---|---|
| Glycerin | 30 g |
| Glucose | 30 g |
| Soluble starch | 20 g |
| Soybean meal | 10 g |
| Gelatin | 2.5 g |
| Yeast extract (Difco) | 2.5 g |
| NH$_4$NO$_3$ | 2.5 g |
| Agar | 3 g |
| Antifoaming agent *1 | 0.1 ml |
| Tap water | 1000 ml |

*1 Nissan Disfoam CB-442 (manufactured by NOF Corp.)
*2 pH was unadjusted 80 ml of a main culture medium having the composition shown in Table 2 below was placed in each of thirteen 500-ml Erlenmeyer flasks, sterilized at 121° C. for 20 minutes, and then cooled to room temperature. 4 ml of the seed culture solution of SANK 10312 was aseptically inoculated to the medium in each flask and cultured for 2 days under conditions of 23° C. and 210 rpm in a rotating shaker. 0.8 ml of a solution of CDDO-Me dissolved at a concentration of 10 mg/ml in dimethyl sulfoxide was added to this culture solution in each flask, and the mixture was cultured again at 210 rpm at 23° C. for 6 days in a rotating shaker.

TABLE 2

| Composition of main culture medium | |
|---|---|
| Glycerin | 30 g |
| Glucose | 30 g |
| Soluble starch | 20 g |
| Soybean flour | 10 g |
| Gelatin | 2.5 g |
| Yeast extract (Difco) | 2.5 g |

TABLE 2-continued

| Composition of main culture medium | |
|---|---|
| NH$_4$NO$_3$ | 2.5 g |
| Antifoaming agent *1 | 0.1 ml |
| Tap water | 1000 ml |

*1 Nissan Disfoam CB-442 (manufactured by NOF Corp.)
*2 pH was unadjusted.

(2) Isolation of Terpenoid Derivative B and Terpenoid Derivative C

The behaviors of terpenoid derivative B and terpenoid derivative C in this Example were monitored by HPLC under conditions given below.

column: Unison UK-C18
(4.6 mm in diameter×75 mm in length; manufactured by Imtakt Corp.)
Solvent:
A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
detection: ultraviolet absorption λ230 nm
Retention Time:
4.9 minutes (terpenoid derivative B)
6.1 minutes (terpenoid derivative C).

To 1040 ml of the culture solution obtained in paragraph (1), an equal amount of acetone was added, and the mixture was allowed to stand at room temperature for 1 hour. Then, the mycelia was removed by suction filtration to obtain 2000 ml of a filtrate. To this filtrate, 1 L of ethyl acetate was added for liquid-liquid distribution to separate an organic layer containing the compounds of interest. The organic layer was washed with saturated saline and dried over anhydrous sodium sulfate, and the solvent was evaporated to dryness to obtain 549.9 mg of a powder containing terpenoid derivative B and terpenoid derivative C. A 275 mg aliquot of this powder was dissolved in 1.37 ml of methanol. A 0.2 ml aliquot of this solution was applied to an HPLC column (Unison US-C18; 20 mm in diameter×150 mm in length; manufactured by Imtakt Corp.) equilibrated in advance with solvents of 0.01% aqueous formic acid solution:acetonitrile containing 0.01% formic acid=45:55, followed by elution at a flow rate of 18.0 ml/min with solvents of 0.01% aqueous formic acid solution:acetonitrile containing 0.01% formic acid=45:55. The ultraviolet absorption of the compounds of interest was detected at a wavelength λ=230 nm. A peak appearing at a retention time of 12.3 minutes (terpenoid derivative B) and a peak appearing at a retention time of 23.9 minutes (terpenoid derivative C) were each separated 7 times. The fraction solutions of each compound were combined and concentrated under reduced pressure, and the obtained suspension was lyophilized to obtain 16.2 mg of terpenoid derivative B as a colorless powder and 2.4 mg of terpenoid derivative C as a colorless powder.

The steric structure of the obtained terpenoid derivative B and terpenoid derivative C of the present invention were determined using two-dimensional nuclear magnetic resonance spectroscopy (NOESY).

In the two-dimensional nuclear magnetic resonance spectroscopy (NOESY) of terpenoid derivative B, the correlation was observed between the proton at the 1-position and the proton of the methyl group at the 10-position and between the β-proton at the 19-position and the β-proton at the 21-position. Its steric structure was therefore determined as represented by the formula (II).

In the two-dimensional nuclear magnetic resonance spectroscopy (NOESY) of terpenoid derivative C, the correlation was observed between the proton at the 1-position and the proton of the methyl group at the 10-position. Its steric structure was therefore determined as represented by the formula (III).

Figure 4:
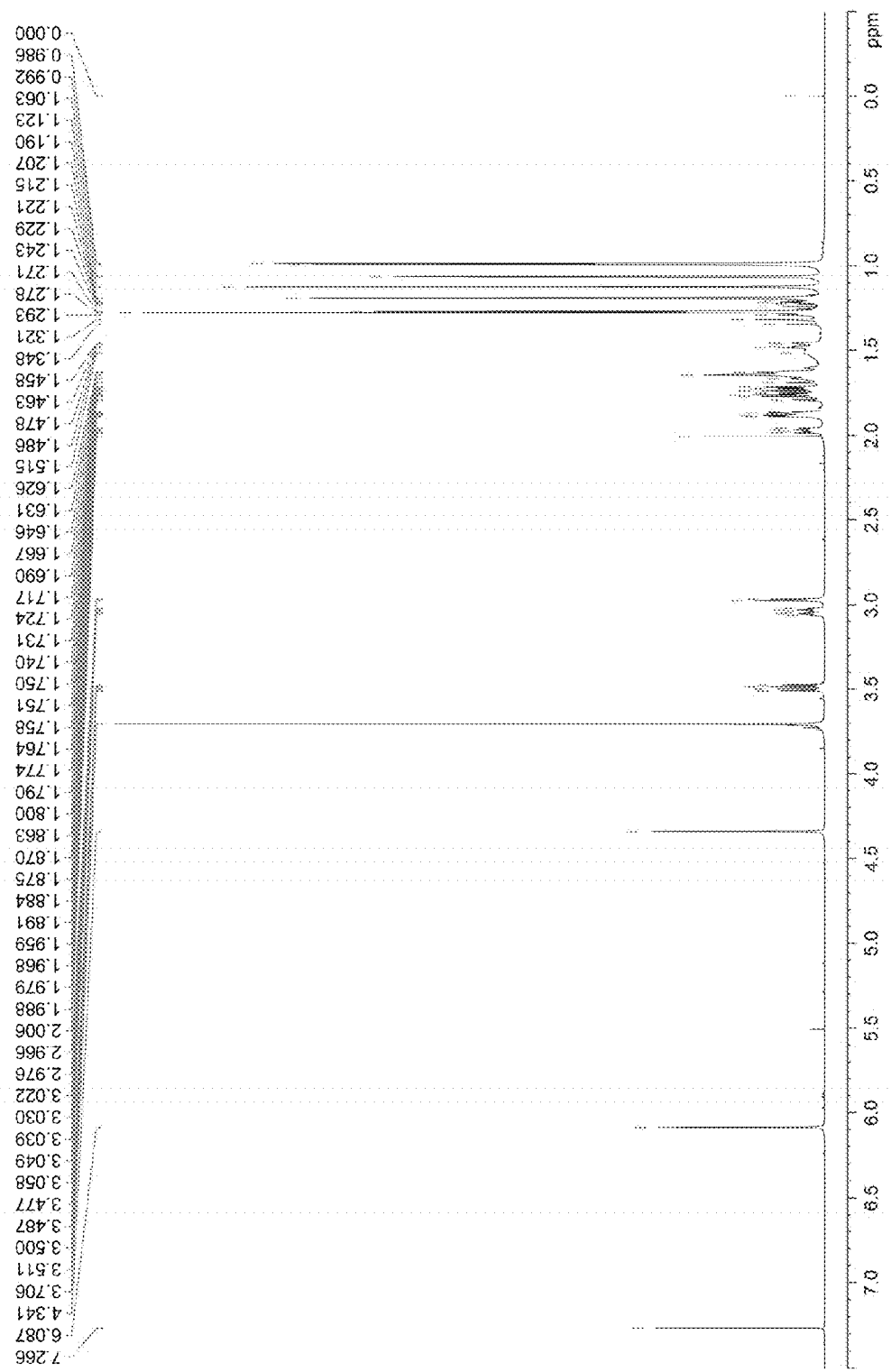
FIG. 4 shows the 1H-NMR spectra of terpenoid derivative B.
Figure 5:
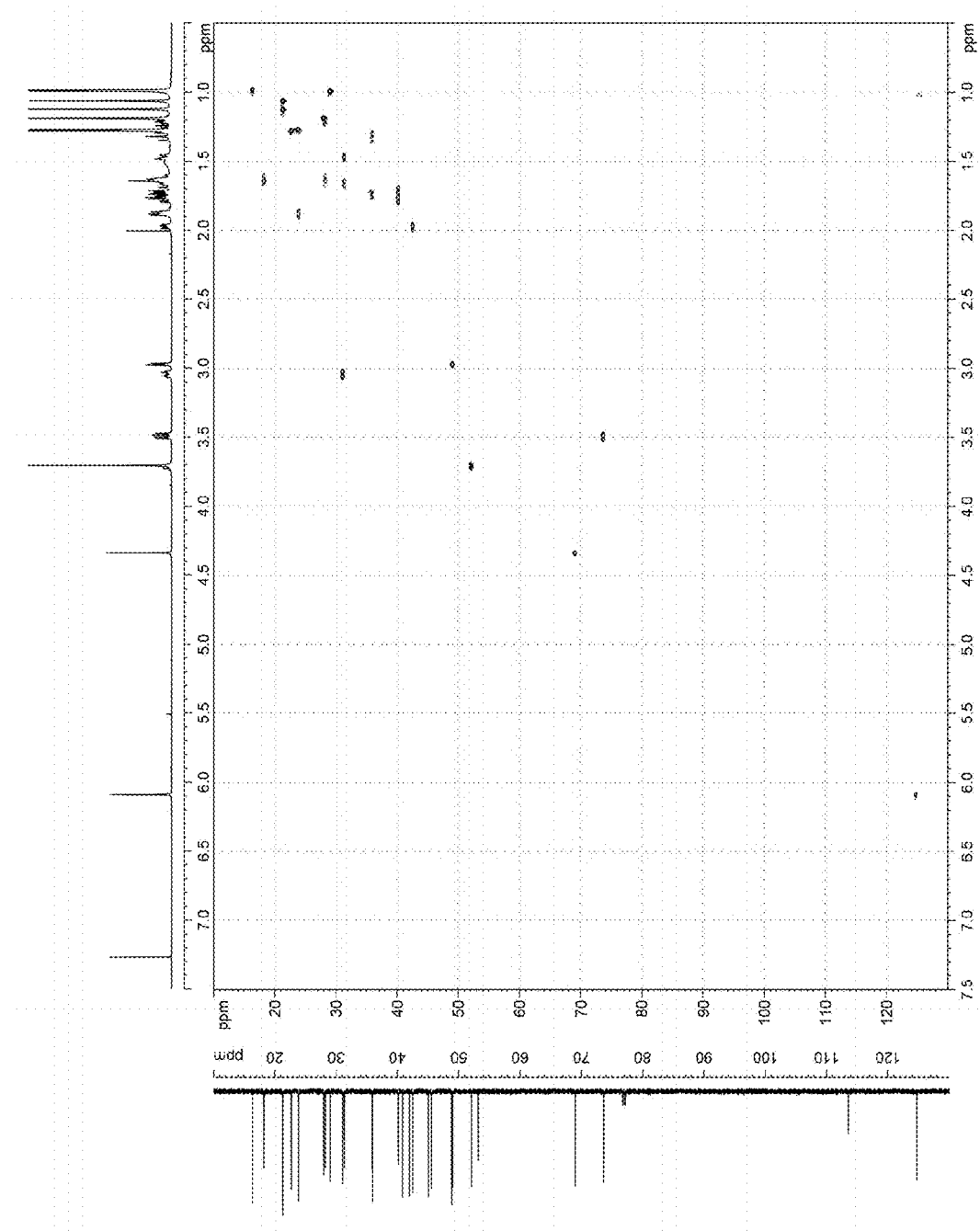
FIG. 5 shows the 1H-13C HSQC spectra of terpenoid derivative B.
Figure 6:
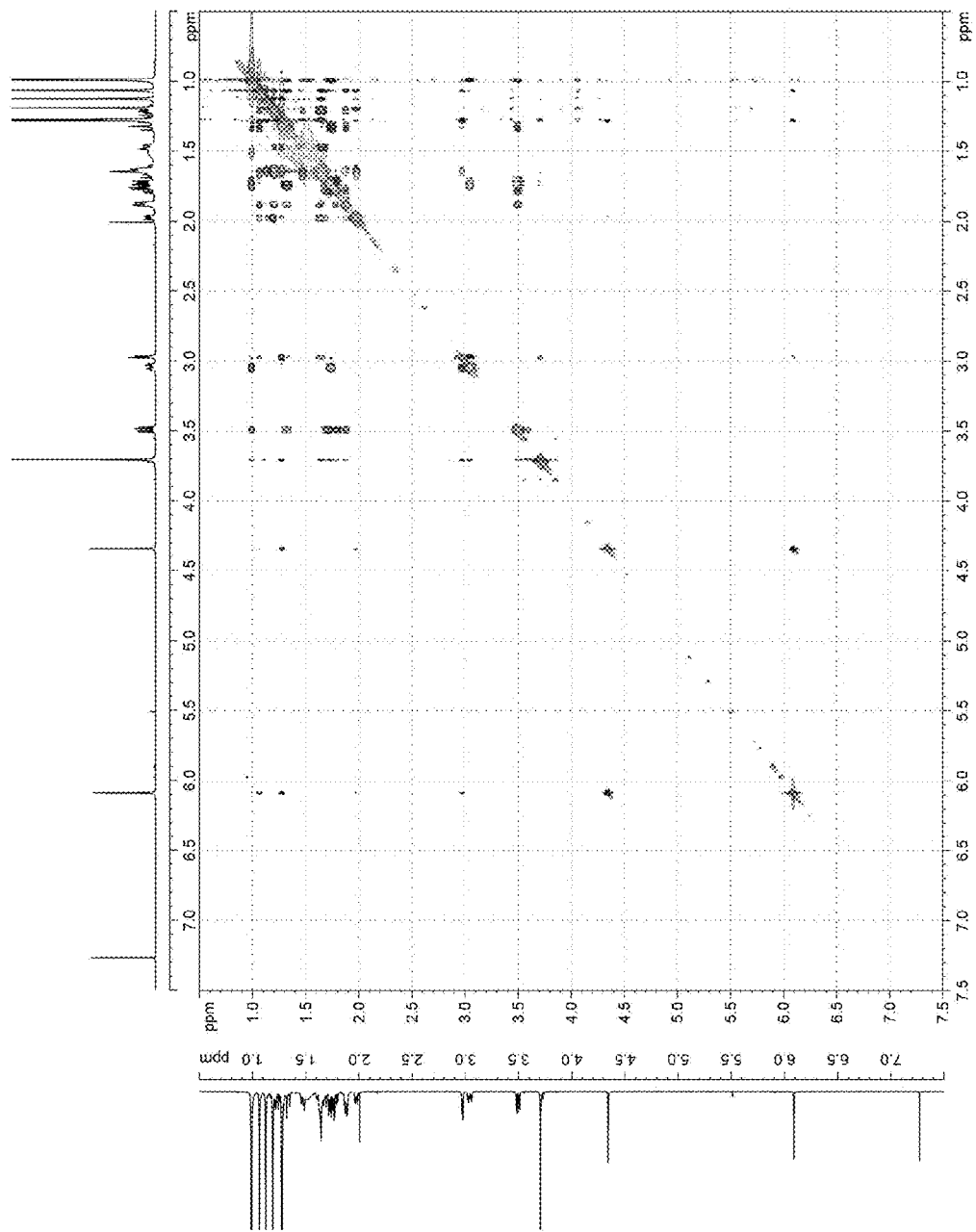
FIG. 6 shows the 1H-1H NOESY spectra of terpenoid derivative B.

Measurement Values of Physicochemical Properties of Terpenoid Derivative B
1) appearance: a colorless powdery substance
2) molecular formula: $C_{32}H_{43}NO_6$
3) molecular weight: 537 (measured by ESI mass spectrometry)
4) the accurate mass, $[M+H]^+$, measured by high-resolution LC-ESI mass spectrometry is as given below:
  found: 538.31573
  calculated: 538.31631
5) $^1$H-nuclear magnetic resonance spectra: the $^1$H-nuclear magnetic resonance spectra (500 MHz) measured with the signal of TMS defined as 0.00 ppm in deuterated chloroform are as given below:
  σ: 0.99 (3H, s), 0.99 (3H, s), 1.06 (3H, s), 1.12 (3H, s), 1.19 (3H, s), 1.19-1.22 (1H, m), 1.27 (3H, s), 1.27 (3H, s), 1.29-1.35 (1H, m), 1.45-1.49 (1H, m), 1.62-1.66 (1H, m), 1.58-1.67 (2H, m), 1.64-1.69 (1H, m), 1.72-1.75 (1H, m), 1.69-1.79 (2H, m), 1.88 (2H, dd, J=10.0 Hz, 3.0 Hz), 1.96 (1H, dd, J=10.0 Hz, 4.5 Hz), 2.97 (1H, s), 3.04 (1H, dd, J=10.0 Hz, 4.5 Hz), 3.49 (1H, dd, J=11.5 Hz, 5.0 Hz), 3.70 (3H, s), 4.34 (1H, s), 6.08 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
  σ: 16.6 (q), 18.5 (t), 21.6 (q×2), 23.0 (q), 24.0 (q), 24.1 (t), 28.2 (q), 28.4 (t), 29.3 (q), 31.3 (d), 31.6 (d), 36.1 (t), 36.2 (s), 40.4 (t), 41.1 (s), 42.2 (s), 42.8 (d), 45.3 (s), 45.8 (s), 49.1 (s), 49.3 (d), 52.3 (s), 53.4 (s), 69.2 (d), 73.9 (t), 113.7 (s), 125.0 (d), 168.9 (s), 176.8 (s), 198.9 (s), 202.5 (s) ppm
7) high-performance liquid chromatography:
column: Unison UK-C18
  (4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=45/55 isocratic
flow rate: 1.0 ml/min
temperature: 40° C.
detection: ultraviolet absorption λ230 nm
retention time: 3.8 minutes
8) The 1H-nuclear magnetic resonance spectra of terpenoid derivative B are shown in FIG. 4, and the two-dimensional nuclear magnetic resonance spectra (1H-13C HSQC spectra) thereof are shown in FIG. 5. As a result of analyzing the 1H-nuclear magnetic resonance spectra and the two-dimensional nuclear magnetic resonance spectra (1H-13C HSQC spectra), each proton was attributed as follows:
  proton at the 1-position: 4.34 ppm (methine)
  proton of the methyl group at the 10-position: 1.27 ppm (methyl)
  β-proton at the 19-position: 1.29 to 1.35 ppm (methine)
  β-proton at the 21-position: 3.49 ppm (methine)
9) The two-dimensional nuclear magnetic resonance spectra (1H-1H NOESY spectra) of terpenoid derivative B are shown in FIG. 6. In FIG. 6, the correlation was observed between the proton at the 1-position and the proton of the methyl group at the 10-position and between the β-proton at the 19-position and the β-proton at the 21-position. Its steric structure was therefore determined as represented by (II).

Figure 7:
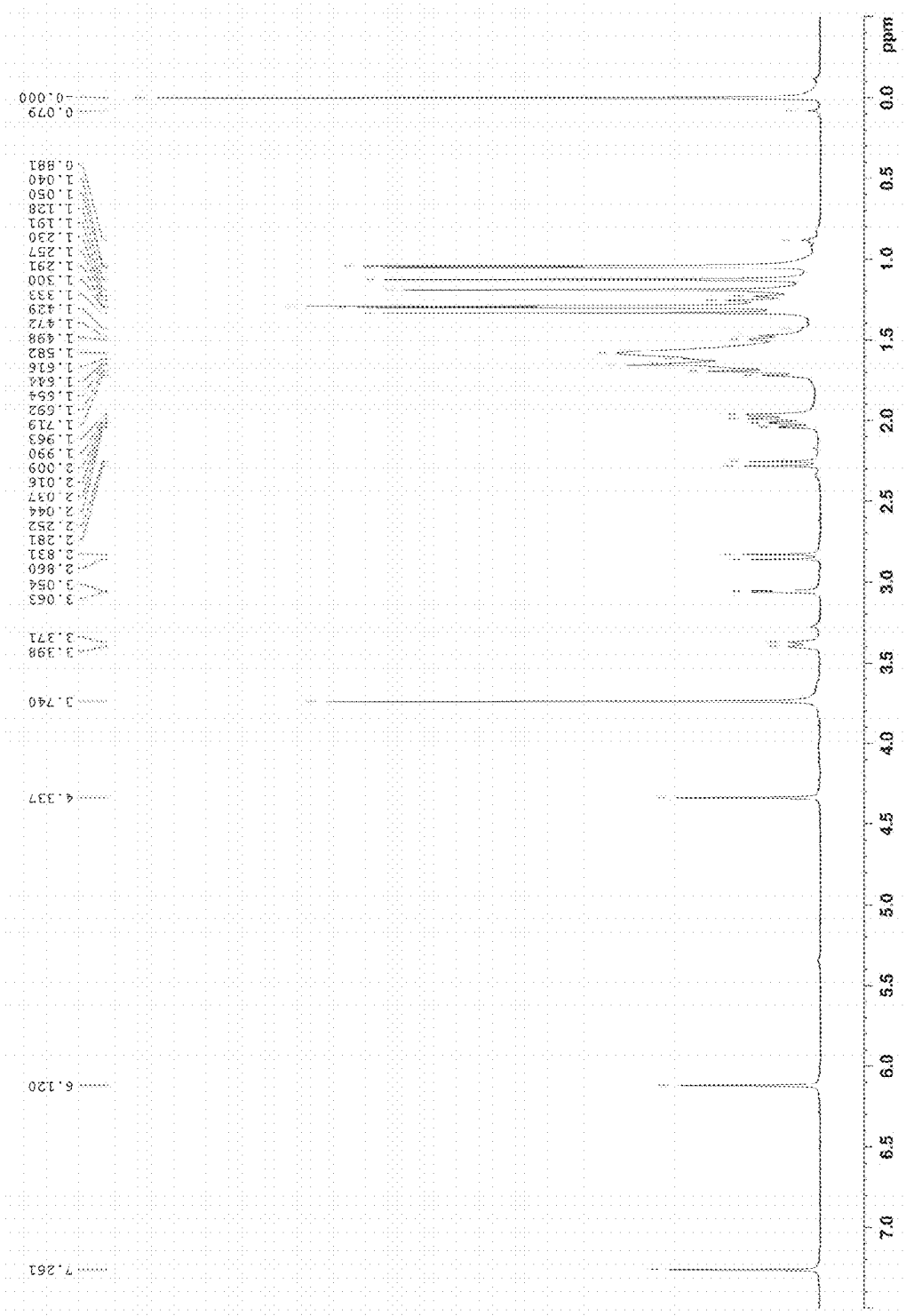
FIG. 7 shows the 1H-NMR spectra of terpenoid derivative C.
Figure 8:
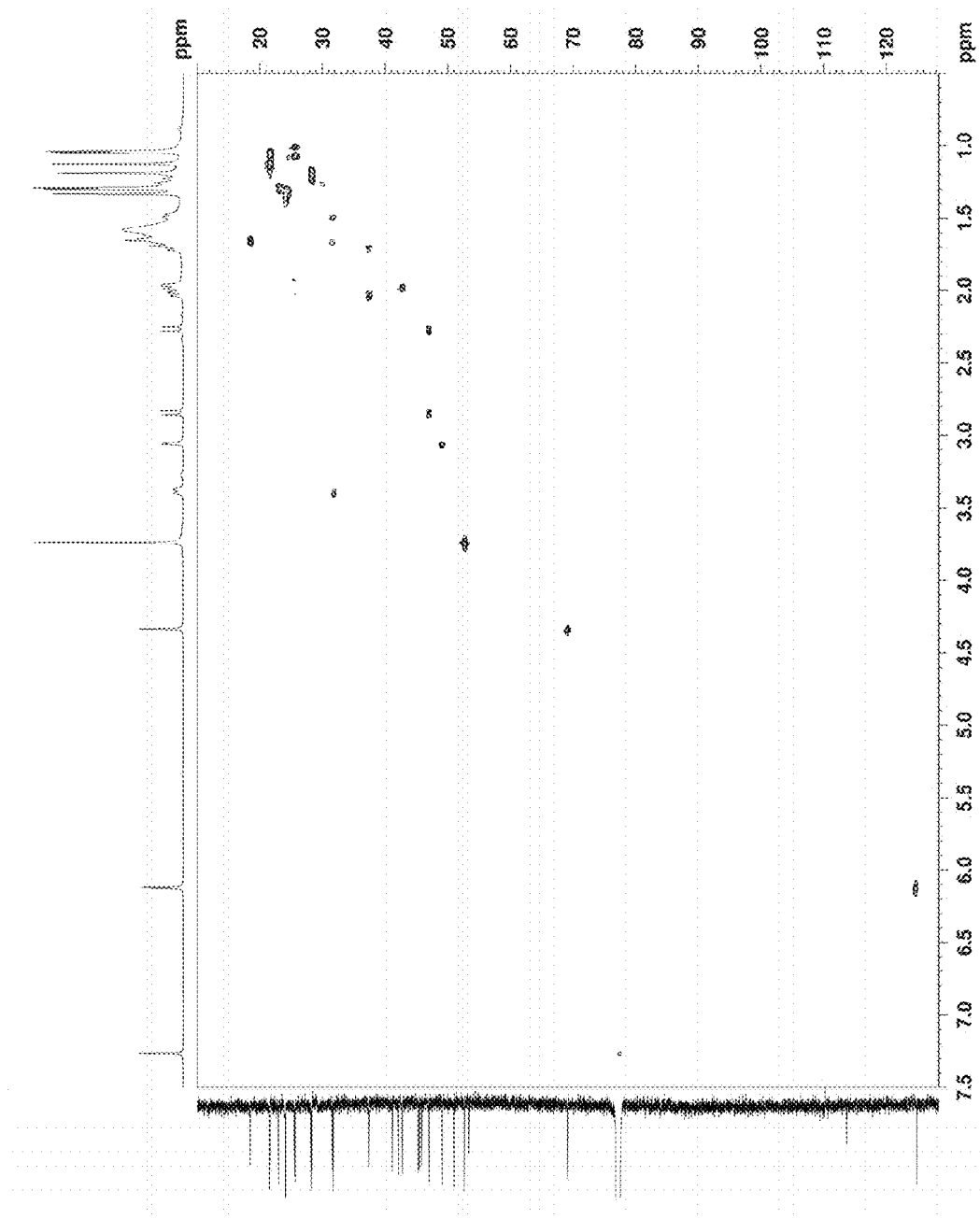
FIG. 8 shows the 1H-13C HSQC spectra of terpenoid derivative C.

Measurement Values of Physicochemical Properties of Terpenoid Derivative C
1) appearance: a colorless powdery substance
2) molecular formula: $C_{32}H_{41}NO_6$
3) molecular weight: 535 (measured by ESI mass spectrometry)
4) the accurate mass, $[M+H]^+$, measured by high-resolution LC-ESI mass spectrometry is as given below:
  found: 536.30023
  calculated: 536.30066
5) $^1$H-nuclear magnetic resonance spectra: the $^1$H-nuclear magnetic resonance spectra (500 MHz) measured with the signal of TMS defined as 0.00 ppm in deuterated chloroform are as given below:
  σ: 1.04 (3H, s), 1.05 (3H, s), 1.13 (3H, s), 1.19 (3H, s), 1.20-1.26 (1H, m), 1.30 (m, 3H), 1.29 (3H, s), 1.33 (3H, s), 1.47-1.50 (1H, m), 1.63-1.68 (2H, m), 1.59-1.68 (2H, m), 1.65-1.67 (1H, m), 1.64-1.73 (2H, m), 1.71 (1H, d, J=13.5 Hz), 1.98 (1H, d, J=13.5 Hz), 2.03 (1H, dd, J=14.0 Hz, 3.5 Hz), 2.27 (1H, d, J=14.5 Hz), 2.85 (1H, d, J=14.5 Hz), 3.05 (1H, d, J=4.5 Hz), 3.38 (1H, brd, J=13.5 Hz), 3.74 (3H, s), 4.34 (1H, s), 6.12 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
  σ: 18.4 (t), 21.6 (q×2), 23.0 (q), 24.1 (q×2), 25.5 (q), 25.6 (t), 28.2 (q), 28.3 (t), 31.5 (t), 31.7 (d), 37.4 (t), 41.2 (s), 42.1 (s), 42.8 (d), 45.3 (s), 45.6 (s), 45.9 (s), 47.0 (t), 49.1 (d), 51.1 (s), 52.7 (q), 53.4 (s), 69.2 (d), 113.7 (s), 124.8 (d), 169.4 (s), 175.5 (s), 198.5 (s), 202.4 (s), 213.4 (s) ppm
7) high-performance liquid chromatography:
column: Unison UK-C18
  (4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=45/55 isocratic
flow rate: 1.0 ml/min
temperature: 40° C.
detection: ultraviolet absorption λ230 nm
retention time: 6.2 minutes
8) The 1H-nuclear magnetic resonance spectra of terpenoid derivative C are shown in FIG. 7, and the two-dimensional nuclear magnetic resonance spectra (1H-13C HSQC spectra) thereof are shown in FIG. 8. As a result of analyzing the 1H-nuclear magnetic resonance spectra and the two-dimensional nuclear magnetic resonance spectra (1H-13C HSQC spectra), each proton was attributed as follows:

proton at the 1-position: 4.34 ppm (methine)
proton of the methyl group at the 10-position: 1.30 ppm (methyl)

Figure 9:
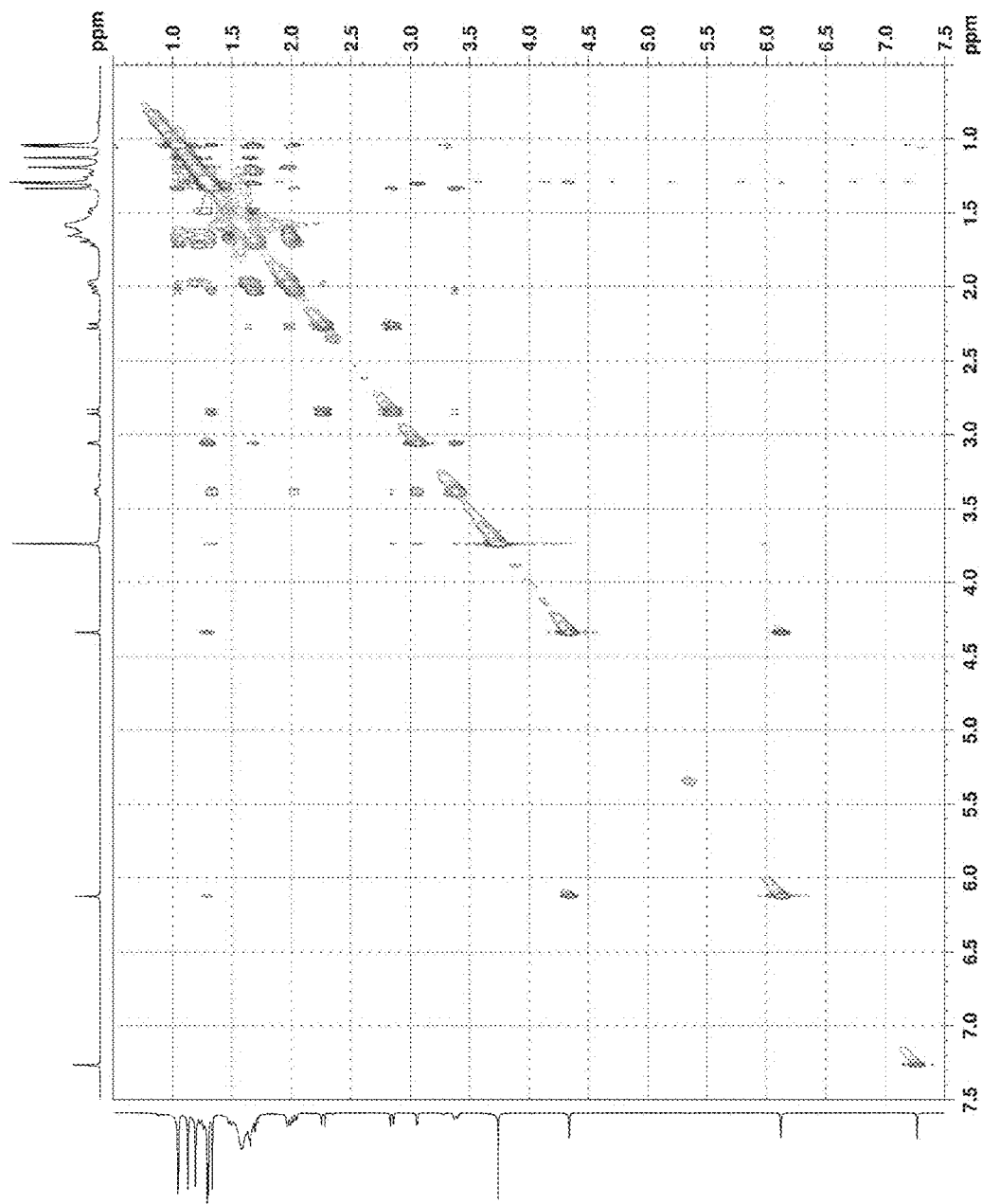
FIG. 9 shows the 1H-1H NOESY spectra of terpenoid derivative C.

9) The two-dimensional nuclear magnetic resonance spectra (1H-1H NOESY spectra) of terpenoid derivative C are shown in FIG. 9. In FIG. 9, the correlation was observed between the proton at the 1-position and the proton of the methyl group at the 10-position. Its steric structure was therefore determined as represented by (III).

Example 2

Production of Terpenoid Derivative B and Terpenoid Derivative C (1) Culture of Strain for Biotransformation of Genus *Mucor*

20 ml of a seed culture medium having the composition shown in Table 1 above was placed in a 100-ml Erlenmeyer flask, sterilized at 121° C. for 20 minutes, and then cooled to room temperature. 1 ml of a spore suspension of SANK 10612 was inoculated to the medium and cultured for 2 days under conditions of 23° C. and 210 rpm in a rotating shaker. Hereinafter, the obtained culture solution is referred to as a "seed culture solution".

80 ml of a main culture medium having the composition shown in Table 2 above was placed in a 500-ml Erlenmeyer flask, sterilized at 121° C. for 20 minutes, and then cooled to room temperature. 4 ml of the seed culture solution of SANK 10612 was aseptically inoculated to the medium and cultured for 2 days under conditions of 23° C. and 210 rpm in a rotating shaker. 0.8 ml of a solution of CDDO-Me dissolved at a concentration of 10 mg/ml in dimethyl sulfoxide was added to this culture solution, and the mixture was cultured again at 210 rpm at 23° C. for 10 days in a rotating shaker.

(2) Isolation of Terpenoid Derivative B and Terpenoid Derivative C

The behaviors of terpenoid derivative B and terpenoid derivative C in this Example were monitored by HPLC under conditions given below.
column: Unison UK-C18
(4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
Retention Time:
  4.9 minutes (terpenoid derivative B)
  6.1 minutes (terpenoid derivative C).

A 1 ml of the culture solution obtained in paragraph (1) was taken out thereof. 0.5 ml of acetonitrile and 0.5 ml of ethanol were added thereto, and the mixture was left standing at room temperature for 1 hour and then centrifuged at 10000 rpm for 10 minutes. The supernatant was used as culture solution extracts.

10 μl of the culture solution extracts thus prepared was subjected to elution under the HPLC conditions described above. The ultraviolet absorption of the compounds of interest was detected at a wavelength λ=230 nm. The transformation efficiency to CDDO-Me was calculated from the peak areas of a peak appearing at a retention time of 4.9 minutes (terpenoid derivative B) and a peak appearing at a retention time of 6.1 minutes (terpenoid derivative C). As a result, the biotransformation efficiency was confirmed to be 10% for terpenoid derivative B and 1% for terpenoid derivative C. The authentic preparations used were terpenoid derivative B and e terpenoid derivative C obtained in Example 1.

Example 3

Production of Terpenoid Derivative A

[Formula 19]

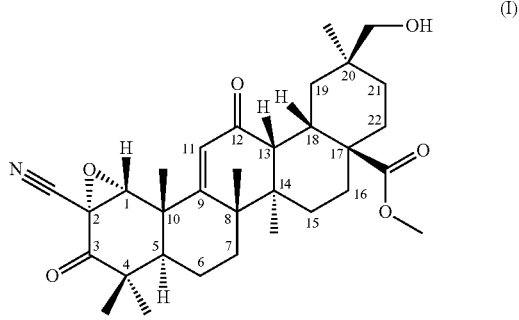

Terpenoid Derivative A (1) Culture of Strain for Biotransformation of Genus *Cunninghamella*

20 ml of a seed culture medium having the composition shown in Table 1 above was placed in each of ten 100-ml Erlenmeyer flasks, sterilized at 121° C. for 20 minutes, and then cooled to room temperature. 1 ml of a spore suspension of SANK 10412 was inoculated to the medium in each flask and cultured for 2 days under conditions of 23° C. and 210 rpm in a rotating shaker. (Hereinafter, the obtained culture solution is referred to as a "seed culture solution").

80 ml of a main culture medium having the composition shown in Table 2 above was placed in each of thirty 500-ml Erlenmeyer flasks, sterilized at 121° C. for 20 minutes, and then cooled to room temperature. 4 ml of the seed culture solution was aseptically inoculated to the medium in each flask and cultured for 2 days under conditions of 23° C. and 210 rpm in a rotating shaker. 0.8 ml of a solution of CDDO-Me dissolved at a concentration of 10 mg/ml in dimethyl sulfoxide was added to this culture solution in each flask, and the mixture was cultured again at 210 rpm at 23° C. for 7 days in a rotating shaker.

(2) Isolation of Terpenoid Derivative A

The behavior of terpenoid derivative A in this Example was monitored by HPLC under conditions given below.
column: Unison UK-C18
   (4.6 mm in diameter×75 mm in length; manufactured by Imtakt Corp.)
Solvent:
   A: 10 mM aqueous ammonium formate solution containing 0.01% formic acid
   B: acetonitrile containing 0.01% formic acid
   A/B=equilibration with 5/5 followed by linear gradient for 7 minutes up to A/B=1/9
flow rate: 1.0 ml/min
temperature: 40° C.
detection: ultraviolet absorption λ230 nm
retention time: 5.9 minutes.

To 2400 ml of the culture solution obtained in paragraph (1), an equal amount of acetone was added, and the mixture was left standing overnight at room temperature. Then, the fungus body was removed by suction filtration to obtain 4500 ml of a filtrate. This filtrate was applied to a Diaion SP207 (150 mL; manufactured by Mitsubishi Chemical Corp.) column equilibrated in advance with water. The column was washed with 600 ml of solvents of distilled water:acetone=5:5, followed by elution with 450 ml of solvents of distilled water:acetone=4:6 and subsequently elution with 900 ml of solvents of distilled water:acetone=7:3. Of the fractions thus obtained, the eluates containing the compound of interest were combined, then concentrated, and subsequently lyophilized to obtain 390.6 mg of a powder containing terpenoid derivative A. This powder was dissolved in 3.9 ml of dimethyl sulfoxide. A 0.5 ml aliquot of this solution was applied to an HPLC column (Unison US-C18; 20 mm in diameter×150 mm in length; manufactured by Imtakt Corp.) equilibrated in advance with solvents of 0.01% aqueous formic acid solution:acetonitrile containing 0.01% formic acid=45:55, followed by elution at a flow rate of 18.0 ml/min with solvents of 0.01% aqueous formic acid solution:acetonitrile containing 0.01% formic acid=45:55. The ultraviolet absorption of the compound of interest was detected at a wavelength λ=230 nm. A peak appearing at a retention time of 16.8 minutes was separated 6 times. The fraction solutions were combined and concentrated under reduced pressure, and the obtained suspension was lyophilized to obtain 1.9 mg of terpenoid derivative A as a colorless powder.

Figure 2:
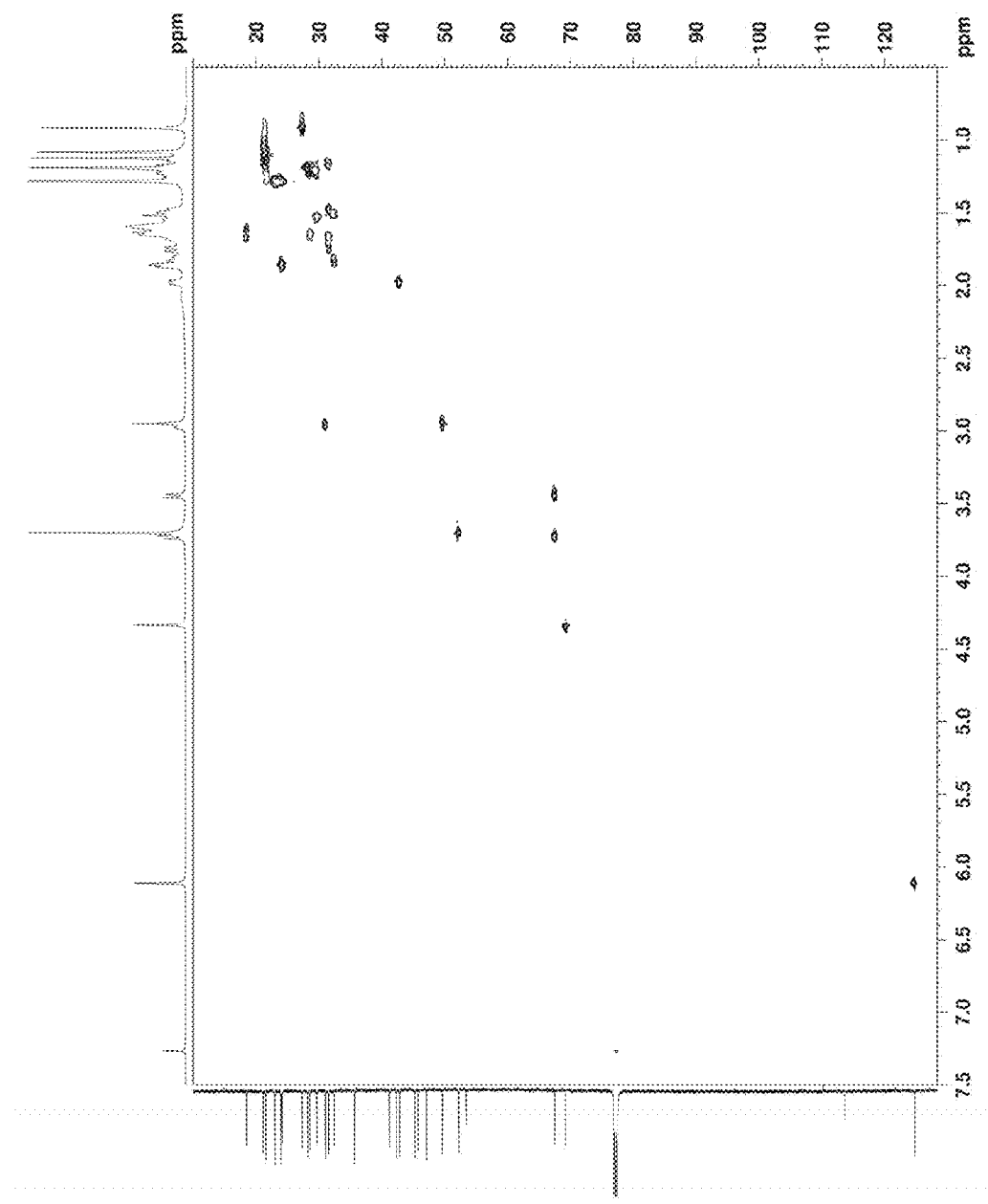
FIG. 2 shows the 1H-13C HSQC spectra of terpenoid derivative A.
Figure 3:
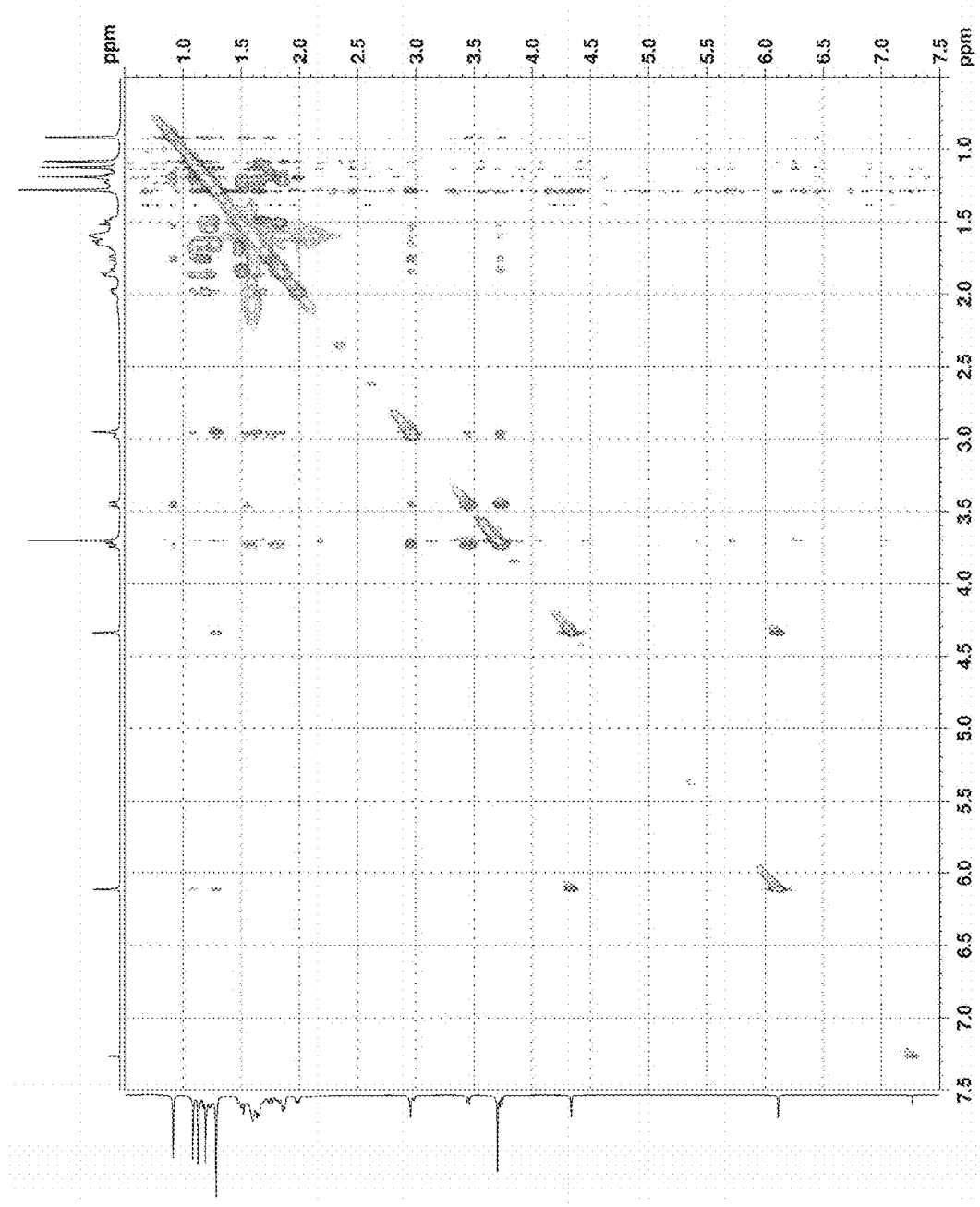
FIG. 3 shows the 1H-1H NOESY spectra of terpenoid derivative A.

Measurement Values of Physicochemical Properties of Terpenoid Derivative A 1) appearance: a colorless powdery substance
2) molecular formula: $C_{32}H_{43}NO_6$
3) molecular weight: 537 (measured by ESI mass spectrometry)
4) the accurate mass, $[M+H]^+$, measured by high-resolution LC-ESI mass spectrometry is as given below:
   found: 538.31549
   calculated: 538.31631
5) $^1$H-nuclear magnetic resonance spectra: the $^1$H-nuclear magnetic resonance spectra (500 MHz) measured with the signal of TMS defined as 0.00 ppm in deuterated chloroform are as given below:
   σ: 0.92 (3H, s), 1.08 (3H, s), 1.12 (3H, s), 1.14-1.17 (1H, m), 1.19 (3H, s), 1.22-1.24 (1H, m), 1.18-1.25 (1H, m), 1.28 (3H, s), 1.28 (3H, s), 1.46-1.48 (1H, m), 1.48-1.52 (1H, m), 1.50-1.54 (1H, m), 1.59-1.67 (2H, m), 1.62-1.66 (1H, m), 1.64-1.67 (1H, m), 1.75 (1H, d, J=13.5 Hz), 1.80-1.83 (1H, m), 1.85-1.87 (2H, m), 1.98 (1H, dd, J=9.0 Hz, 4.5 Hz), 2.95 (1H, s), 2.98 (1H, brs), 3.45 (1H, d, J=11.5 Hz), 3.70 (3H, s), 3.73 (1H, d, J=11.5 Hz), 4.34 (1H, s), 6.11 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
   σ: 18.5 (t), 21.1 (q), 21.6 (q), 23.0 (q), 24.0 (q), 24.1 (t), 27.3 (q), 28.2 (q), 28.6 (t), 29.6 (t), 31.0 (d), 31.5 (t), 31.6 (t), 32.4 (t), 35.7 (s), 41.2 (s), 42.3 (s), 42.8 (d), 45.3 (s), 45.8 (s), 47.1 (s), 49.6 (d), 52.3 (q), 53.5 (s), 67.6 (t), 69.3 (d), 113.7 (s), 124.8 (d), 169.8 (s), 178.0 (s), 199.6 (s), 202.5 (s) ppm
7) high-performance liquid chromatography:
column: Unison UK-C18
   (4.6 mm in diameter×75 mm in length; manufactured by Imtakt Corp.)
Solvent:
   A: 10 mM aqueous ammonium formate solution containing 0.01% formic acid
   B: acetonitrile containing 0.01% formic acid
   A/B=45/55 isocratic
flow rate: 1.0 ml/min
temperature: 40° C.
detection: ultraviolet absorption λ230 nm
retention time: 5.8 minutes
8) The 1H-nuclear magnetic resonance spectra of terpenoid derivative A are shown in FIG. 1, and the two-dimensional nuclear magnetic resonance spectra (1H-13C HSQC spectra) thereof are shown in FIG. 2. As a result of analyzing the 1H-nuclear magnetic resonance spectra and the two-dimensional nuclear magnetic resonance spectra (1H-13C HSQC spectra), each proton was attributed as follows:
   proton at the 1-position: 4.34 ppm (methine)
   proton of the methyl group at the 10-position: 1.28 ppm (methyl)
   proton at the 18-position: 2.98 ppm (methine)
   methylene proton of the hydroxymethyl group at the 20-position: 3.73 ppm, 3.45 ppm (methylene)
9) The two-dimensional nuclear magnetic resonance spectra (1H-1H NOESY spectra) of terpenoid derivative A are shown in FIG. 3. In FIG. 3, correlation was observed between the proton at the 1-position and the proton of the methyl group at the 10-position and between the α-proton at the 18-position and the methylene proton of the hydroxymethyl group at the 20-position. Its steric structure was therefore determined as represented by (I).

Example 4

Production of Terpenoid Derivative D

[Formula 20]

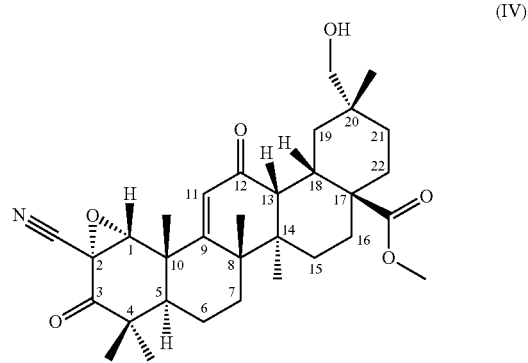

(IV)

Terpenoid Derivative D (1) Culture of Strain for Biotransformation of Genus *Cunninghamella*

20 ml of a seed culture medium having the composition shown in Table 1 above was placed in each of ten 100-ml Erlenmeyer flasks, sterilized at 121° C. for 20 minutes, and then cooled to room temperature. 1 ml of a spore suspension of SANK 10412 was inoculated to the medium in each flask and cultured for 2 days under conditions of 23° C. and 210 rpm in a rotating shaker. Hereinafter, the obtained culture solution is referred to as a "seed culture solution".

80 ml of a main culture medium having the composition shown in Table 2 above was placed in each of thirty 500-ml Erlenmeyer flasks, sterilized at 121° C. for 20 minutes, and then cooled to room temperature. 4 ml of the seed culture solution was aseptically inoculated to the medium in each flask and cultured for 2 days under conditions of 23° C. and 210 rpm in a rotating shaker. 0.8 ml of a solution of CDDO-Me dissolved at a concentration of 10 mg/ml in dimethyl sulfoxide was added to this culture solution in each flask, and the mixture was cultured again at 210 rpm at 23° C. for 7 days in a rotating shaker.

(2) Isolation of Terpenoid Derivative D

The behavior of terpenoid derivative D in this Example was monitored by HPLC under conditions given below.
column: Unison UK-C18
(4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 5.2 minutes.

To 2400 ml of the culture solution obtained in paragraph (1), an equal amount of acetone was added, and the mixture was allowed to stand overnight at room temperature. Then, the mycelia was removed by suction filtration to obtain 4500 ml of a filtrate. This filtrate was applied to a Diaion SP207 (150 mL; manufactured by Mitsubishi Chemical Corp.) column equilibrated in advance with water. The column was washed with 1000 ml of solvents of distilled water:acetone=5:5, followed by elution with 450 ml of solvents of distilled water:acetone=4:6 and subsequently elution with 900 ml of solvents of distilled water:acetone=7:3. Of the fractions thus obtained, the fractions containing the compound of interest were combined, then concentrated, and subsequently lyophilized to obtain 390.6 mg of extracts containing terpenoid derivative D. This powder was dissolved in 3.9 ml of dimethyl sulfoxide. A 0.5 ml of this solution was applied to an HPLC column (Unison US-C18; 20 mm in diameter×150 mm in length; manufactured by Imtakt Corp.) equilibrated in advance with solvents of 0.01% aqueous formic acid solution:acetonitrile containing 0.01% formic acid=45:55, followed by elution at a flow rate of 18.0 ml/min with solvents of 0.01% aqueous formic acid solution:acetonitrile containing 0.01% formic acid=45:55. The ultraviolet absorption of the compound of interest was detected at a wavelength λ=230 nm. A peak appearing at a retention time of 12.8 minutes (terpenoid derivative D) was separated 6 times. The fraction solutions were combined and concentrated under reduced pressure, and the obtained suspension was lyophilized to obtain 8.8 mg of terpenoid derivative D as a colorless powder.

Figure 10:
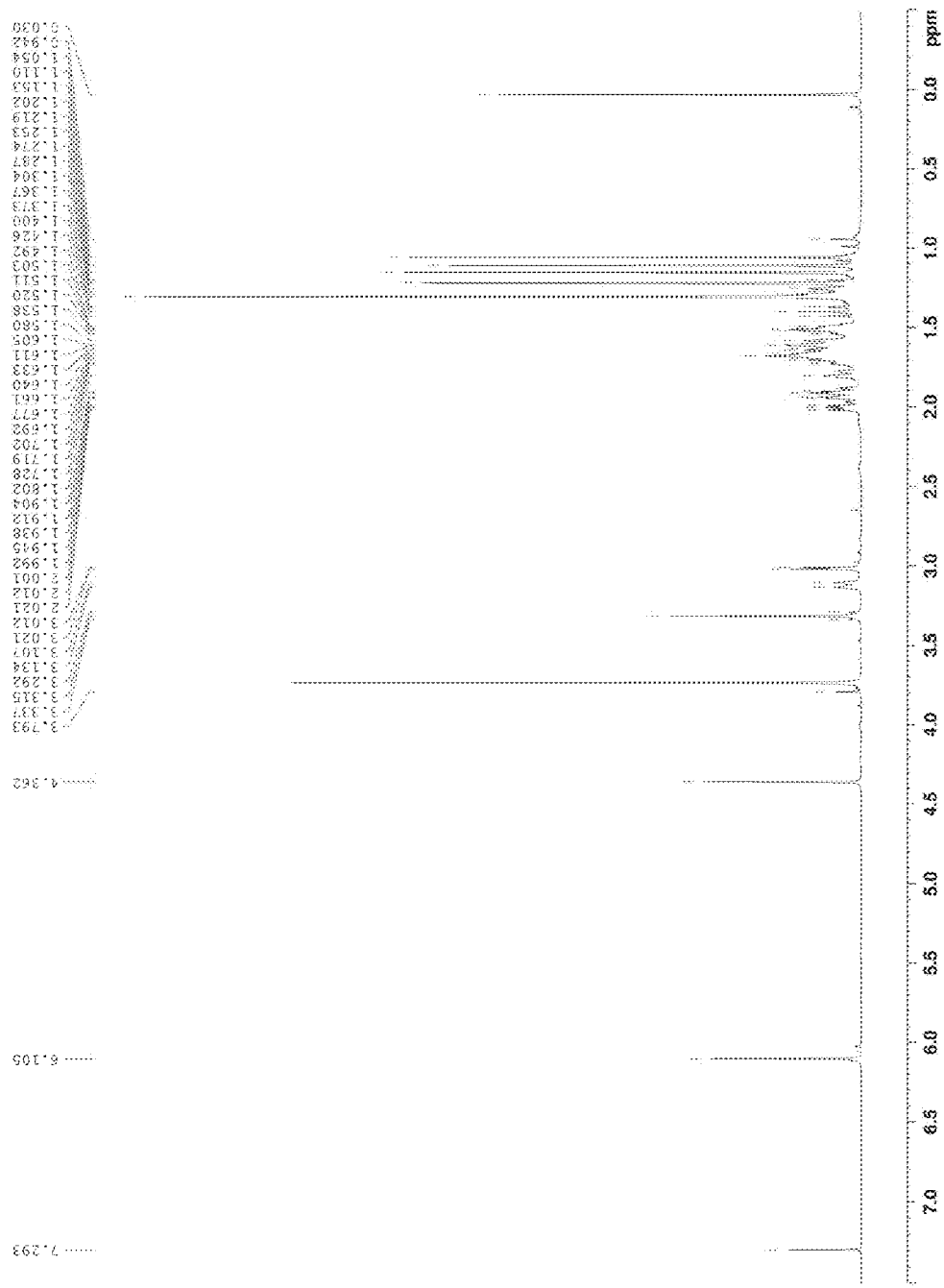
FIG. 10 shows the 1H-NMR spectra of terpenoid derivative D.
Figure 11:
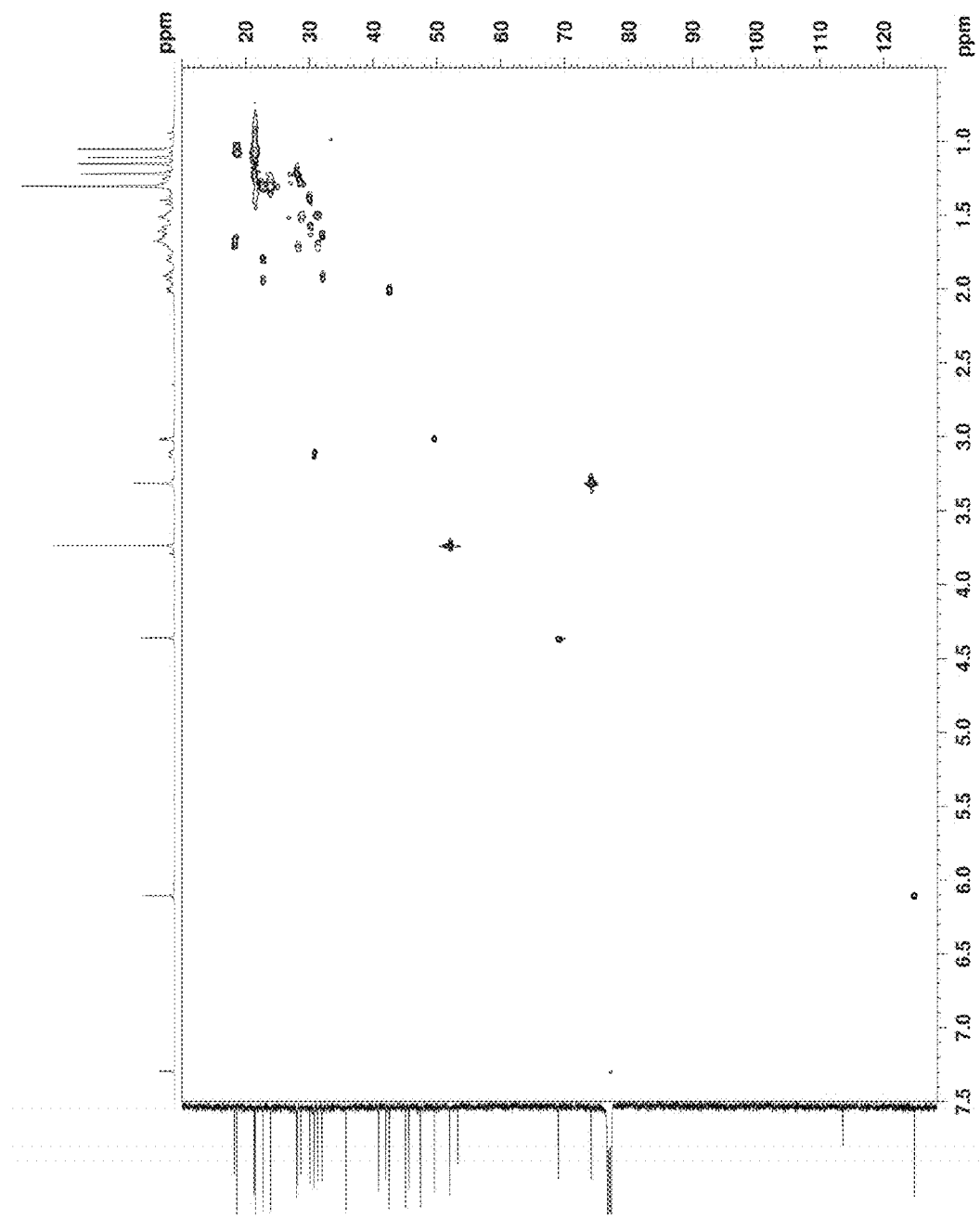
FIG. 11 shows the 1H-13C HSQC spectra of terpenoid derivative D.
Figure 12:
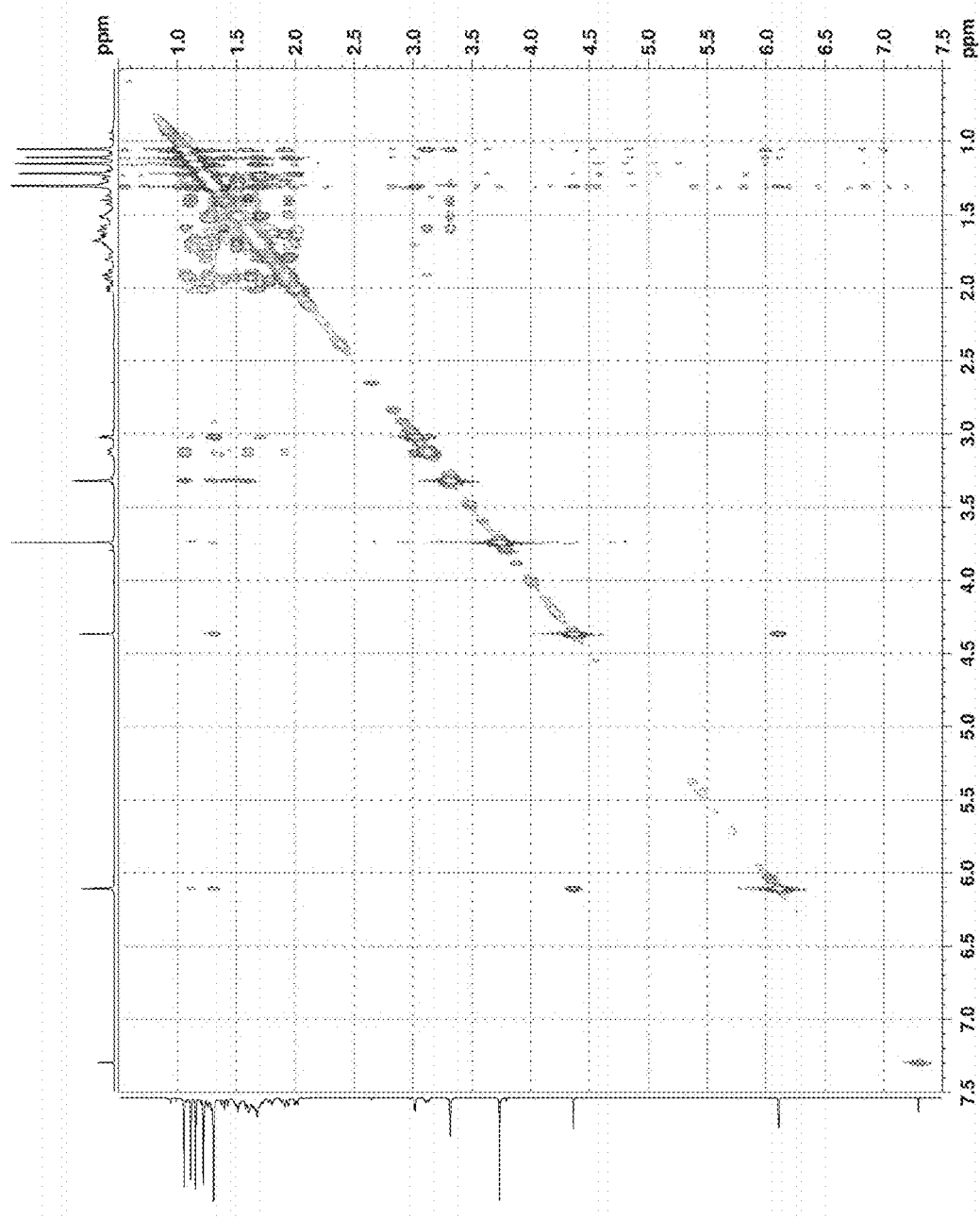
FIG. 12 shows the 1H-1H NOESY spectra of terpenoid derivative D

Measurement Values of Physicochemical Properties of Terpenoid Derivative D 1) appearance: a colorless powdery substance
2) molecular formula: $C_{32}H_{43}NO_6$
3) molecular weight: 537 (measured by ESI mass spectrometry)
4) the accurate mass, $[M+H]^+$, measured by high-resolution LC-ESI mass spectrometry is as given below:
   found: 538.31592
   calculated: 538.31631
5) $^1$H-nuclear magnetic resonance spectra: the $^1$H-nuclear magnetic resonance spectra (500 MHz) measured with the signal of TMS defined as 0.00 ppm in deuterated chloroform are as given below:
   σ: 1.05 (3H, s), 1.11 (3H, s), 1.15 (3H, s), 1.22 (3H, s), 1.25-1.27 (1H, m), 1.27-1.29 (1H, m), 1.30 (3H, s), 1.30 (3H, s), 1.40 (1H, brt, J=13.0 Hz), 1.48-1.52 (1H, m), 1.50-1.54 (1H, m), 1.58-1.60 (1H, m), 1.60-1.63 (1H, m), 1.62-1.71 (2H, m), 1.66-1.70 (1H, m), 1.69-1.73 (1H, m), 1.76-1.82 (1H, m), 1.90-1.94 (1H, m), 1.93-1.99 (1H, m), 2.01 (1H, dd, J=4.5 Hz, 10.0 Hz), 3.02 (1H, d, J=4.5 Hz), 3.12 (1H, dt, J=3.5 Hz, 13.5 Hz), 3.32 (3H, s), 3.74 (3H, s), 4.36 (1H, s), 6.11 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
   σ: 18.3 (t), 18.7 (q), 21.4 (q), 21.5 (q), 22.7 (t), 22.8 (q), 23.9 (q), 28.0 (q), 28.2 (t), 28.7 (t), 30.1 (t), 30.8 (d), 31.4 (t), 32.0 (t), 35.8 (s), 40.9 (s), 42.0 (s), 42.5 (d), 45.1 (s), 45.6 (s), 47.4 (s), 49.6 (d), 52.0 (q), 53.2 (s), 69.1 (d), 74.2 (t), 113.6 (s), 124.8 (d), 168.7 (s), 178.0 (s), 198.7 (s), 202.4 (s) ppm
7) high-performance liquid chromatography:
column: Unison UK-C18
(4.6 mm in diameter×75 mm in length; manufactured by Imtakt Corp.)
solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 5.2 minutes
8) The 1H-nuclear magnetic resonance spectra of terpenoid derivative D are shown in FIG. 10, and the two-dimensional nuclear magnetic resonance spectra (1H-13C HSQC spectra) thereof are shown in FIG. 11. As a result of analyzing the 1H-nuclear magnetic resonance spectra and the two-dimensional nuclear magnetic resonance spectra (1H-13C HSQC spectra), each proton was attributed as follows:
   proton at the 1-position: 4.36 ppm (methine)
   proton of the methyl group at the 10-position: 1.30 ppm
   α-proton at the 18-position: 3.12 ppm (methine)
   proton of the methyl group at the 20-position: 1.05 ppm (methylene)
9) The two-dimensional nuclear magnetic resonance spectra (1H-1H NOESY spectra) of terpenoid derivative D are shown in FIG. 12. In FIG. 12, correlation was observed between the proton at the 1-position and the proton of the methyl group bonded to the 10-position and between the α-proton at the 18-position and the proton of the methyl group at the 20-position. Its steric structure was therefore determined as represented by (IV).

Example 5

Production of Terpenoid Derivative H

[Formula 21]

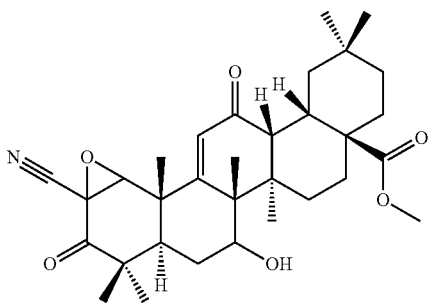

Terpenoid Derivative H (1) Culture of Strain for Biotransformation of Genus *Cunninghamella*

20 ml of a seed culture medium having the composition shown in Table 1 above was placed in each of ten 100-ml Erlenmeyer flasks, sterilized at 121° C. for 20 minutes, and then cooled to room temperature. 1 ml of a spore suspension of SANK 10412 was inoculated to the medium in each flask and cultured for 2 days under conditions of 23° C. and 210 rpm in a rotating shaker. (Hereinafter, the obtained culture solution is referred to as a "seed culture solution".)

80 ml of a main culture medium having the composition shown in Table 2 above was placed in each of thirty 500-ml Erlenmeyer flasks, sterilized at 121° C. for 20 minutes, and then cooled to room temperature. 4 ml of the seed culture solution was aseptically inoculated to the medium in each flask and cultured for 2 days under conditions of 23° C. and 210 rpm in a rotating shaker. 0.8 ml of a solution of CDDO-Me dissolved at a concentration of 10 mg/ml in dimethyl sulfoxide was added to this culture solution in each flask, and the mixture was cultured again at 210 rpm at 23° C. for 7 days in a rotating shaker.

(2) Isolation of Terpenoid Derivative H

The behavior of terpenoid derivative H in this Example was monitored by HPLC under conditions given below.
column: Unison UK-C18
(4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 6.0 minutes.

To 2400 ml of the culture solution obtained in paragraph (1), an equal amount of acetone was added, and the mixture was allowed to stand overnight at room temperature. Then, the mycelia was removed by suction filtration to obtain 4500 ml of a filtrate. This filtrate was applied to a Diaion SP207 (150 mL; manufactured by Mitsubishi Chemical Corp.) column equilibrated in advance with water. The column was washed with 1000 ml of solvents of distilled water:acetone=5:5, followed by elution with 450 ml of solvents of distilled water:acetone=4:6 and subsequently elution with 900 ml of solvents of distilled water:acetone=7:3. Of the fractions thus obtained, the fractions containing the compound of interest were combined, then concentrated, and subsequently lyophilized to obtain 390.6 mg of extracts containing terpenoid derivative H. This powder was dissolved in 3.9 ml of dimethyl sulfoxide. A 0.5 ml of this solution was applied to an HPLC column (Unison US-C18; 20 mm in diameter×150 mm in length; manufactured by Imtakt Corp.) equilibrated in advance with solvents of 0.01% aqueous formic acid solution:acetonitrile containing 0.01% formic acid=45:55, followed by elution at a flow rate of 18.0 ml/min with solvents of 0.01% aqueous formic acid solution:acetonitrile containing 0.01% formic acid=45:55. The ultraviolet absorption of the compound of interest was detected at a wavelength λ=230 nm. A peak appearing at a retention time of 20.0 minutes (terpenoid derivative H) was separated 6 times. The fraction solutions were combined and concentrated under reduced pressure, and the obtained suspension was lyophilized to obtain 14.1 mg of terpenoid derivative H as a colorless powder.

Measurement Values of Physicochemical Properties of Terpenoid Derivative H 1) appearance: a colorless powdery substance
2) molecular formula: $C_{32}H_{43}NO_6$
3) molecular weight: 537 (measured by ESI mass spectrometry)
4) the accurate mass, $[M+H]^+$, measured by high-resolution LC-ESI mass spectrometry is as given below:
   found: 538.31543
   calculated: 538.31631
5) $^1$H-nuclear magnetic resonance spectra: the $^1$H-nuclear magnetic resonance spectra (500 MHz) measured with the signal of TMS defined as 0.00 ppm in deuterated chloroform are as given below:
   σ: 0.90 (3H, s), 1.00 (3H, s), 1.13 (3H, s), 1.13 (3H, s), 1.20 (3H, s), 1.28 (3H, s), 1.22-1.24 (1H, m), 1.23-1.27 (1H, m), 1.30 (3H, s), 1.31-1.34 (1H, m), 1.39-1.41 (1H, m), 1.52-1.55 (1H, m), 1.58-1.60 (1H, m), 1.67-1.70 (1H, m), 1.73-1.78 (1H, m), 1.74-1.76 (1H, m), 1.82 (1H, dd, J=5.0 Hz, 14.0 Hz), 1.90-1.93 (1H, m), 1.93-1.95 (1H, m), 2.01 (1H, dd, J=2.0 Hz, 13.5 Hz), 2.99 (1H, d, J=4.5 Hz), 3.06 (1H, brd, J=13.5 Hz), 3.71 (3H, s), 4.07 (1H, brd, J=5.5 Hz), 4.30 (1H, s), 6.08 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
   σ: 19.3 (q), 21.7 (q), 22.46 (q), 22.48 (q), 23.1 (t), 23.3 (q), 28.2 (q), 28.8 (t), 30.9 (s), 31.6 (t), 31.8 (d), 33.5 (q), 34.7 (t), 36.2 (t), 39.8 (d), 41.3 (s), 43.5 (s), 45.0 (s), 47.3 (s), 49.7 (d), 51.2 (s), 52.2 (q), 53.4 (s), 69.1 (d), 70.7 (d), 113.6 (s), 125.8 (d), 168.7 (s), 178.3 (s), 198.8 (s), 202.0 (s) ppm
7) high-performance liquid chromatography:
column: Unison UK-C18
(4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 6.0 minutes.

Example 6

Production of Terpenoid Derivative E

[Formula 22]

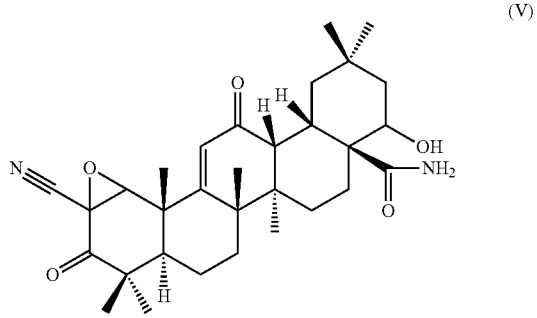

(V)

Terpenoid Derivative E (1) Culture of Strain for Biotransformation of Genus *Chaetomium*

20 ml of a seed culture medium having the composition shown in Table 1 above was placed in a 100-ml Erlenmeyer flask, sterilized at 121° C. for 20 minutes, and then cooled to room temperature. 1 ml of a spore suspension of SANK 10312 strain was inoculated to the medium in the flask and cultured for 2 days under conditions of 23° C. and 210 rpm in a rotating shaker. (Hereinafter, the obtained culture solution is referred to as a "seed culture solution".)

80 ml of a main culture medium having the composition shown in Table 2 above was placed in a 500-ml Erlenmeyer flask, sterilized at 121° C. for 20 minutes, and then cooled to room temperature. 4 ml of the seed culture solution of SANK 10312 strain was aseptically inoculated to the medium in the flask and cultured for 2 days under conditions of 23° C. and 210 rpm in a rotating shaker. 0.8 ml of a solution of the compound (IX) dissolved at a concentration of 10 mg/ml in dimethyl sulfoxide was added to this culture solution in the flask, and the mixture was cultured again at 210 rpm at 23° C. for 7 days in a rotating shaker.

(2) Isolation of Terpenoid Derivative E

The behavior of terpenoid derivative E in this Example was monitored by HPLC under conditions given below.
column: Unison UK-C18
(4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 3.2 minutes (terpenoid derivative E).

To 80 ml of the culture solution obtained in paragraph (1), an equal amount of acetone was added, and the mixture was allowed to stand overnight at room temperature. Then, the mycelia was removed by suction filtration to obtain 150 ml of a filtrate. To this filtrate, 80 ml of ethyl acetate was added for liquid-liquid distribution to separate an organic layer containing the compound of interest. The organic layer was washed with saturated saline and dried over anhydrous sodium sulfate, and the solvent was evaporated to dryness to obtain 62.1 mg of a residue containing terpenoid derivative E. This powder was dissolved in 0.62 ml of dimethyl sulfoxide. A 0.3 ml of this solution was applied to an HPLC column (Unison US-C18; 20 mm in diameter×150 mm in length; manufactured by Imtakt Corp.) equilibrated in advance with solvents of 0.01% aqueous formic acid solution:acetonitrile containing 0.01% formic acid=60:40, followed by isocratic development for 20 minutes with solvents of 0.01% aqueous formic acid solution:acetonitrile containing 0.01% formic acid=60:40, then development in a linear gradient for 20 minutes up to a solvent ratio of 0.01% aqueous formic acid solution:acetonitrile containing 0.01% formic acid=10:90, and elution at a flow rate of 18.0 ml/min. The ultraviolet absorption of the compound of interest was detected at a wavelength λ=230 nm. A peak appearing at a retention time of 19.0 minutes (terpenoid derivative E) was separated 2 times. The fraction solutions were combined and concentrated under reduced pressure, and the obtained suspension was lyophilized to obtain 0.95 mg of terpenoid derivative E as a colorless powder.

Measurement Values of Physicochemical Properties of Terpenoid Derivative E 1) appearance: a colorless powdery substance
2) molecular formula: $C_{31}H_{42}N_2O_5$
3) molecular weight: 522 (measured by ESI mass spectrometry)
4) the accurate mass, $[M+H]^+$, measured by high-resolution LC-ESI mass spectrometry is as given below:
  found: 523.31616
  calculated: 523.31665
5) $^1$H-nuclear magnetic resonance spectra: the $^1$H-nuclear magnetic resonance spectra (500 MHz) measured with the signal of TMS defined as 0.00 ppm in deuterated chloroform are as given below:
  σ: 0.95 (3H, s), 1.03 (3H, s), 1.10 (3H, s), 1.13 (3H, s), 1.19 (3H, s), 1.26-1.30 (1H, m), 1.28-1.30 (1H, m), 1.28 (3H, s), 1.34 (3H, s), 1.35 (1H, t, J=12.5 Hz), 1.48-1.52 (1H, m), 1.57-1.60 (1H, m), 1.60-1.68 (2H, m), 1.64-1.68 (1H, m), 1.65-1.69 (1H, m), 1.72-1.74 (1H, m), 1.79-1.81 (1H, m), 1.97-1.99 (1H, m), 1.98-2.00 (1H, m), 2.92 (1H, brd, J=13.0 Hz), 3.42 (1H, d, J=4.0 Hz), 3.90 (1H, brd, J=10.0 Hz), 4.34 (1H, s), 6.08 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
  σ: 17.4 (t), 18.3 (t), 21.4 (q), 21.5 (q), 22.8 (q), 24.0 (q), 24.2 (q), 27.7 (t), 28.0 (q), 31.1. (s), 31.4 (t), 31.8 (d), 33.2 (q), 35.6 (t), 40.9 (s), 42.58 (d), 42.62 (s), 43.8 (t), 45.1 (s), 45.8 (s), 49.2 (d), 51.6 (s), 53.3 (s), 69.1 (d), 71.0 (d), 113.6 (s), 124.8 (d), 168.7 (s), 178.7 (s), 198.8 (s), 202.3 (s) ppm
7) high-performance liquid chromatography:
column: Unison UK-C18
(4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 3.2 minutes.

Example 7

Production of Terpenoid Derivative F

[Formula 23]

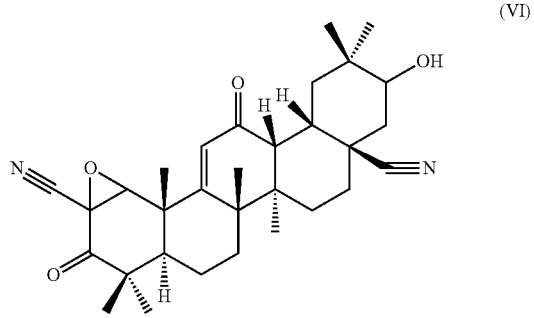

(VI)

Terpenoid Derivative F (1) Culture of Strain for Biotransformation of Genus *Chaetomium*

20 ml of a seed culture medium having the composition shown in Table 1 above was placed in each of ten 100-ml Erlenmeyer flasks, sterilized at 121° C. for 20 minutes, and then cooled to room temperature. 1 ml of a spore suspension of SANK 10312 was inoculated to the medium in each flask and cultured for 2 days under conditions of 23° C. and 210 rpm in a rotating shaker. (Hereinafter, the obtained culture solution is referred to as a "seed culture solution").

80 ml of a main culture medium having the composition shown in Table 2 above was placed in each of thirty-three 500-ml Erlenmeyer flasks, sterilized at 121° C. for 20 minutes, and then cooled to room temperature. 4 ml of the seed culture solution of SANK 10312 strain was aseptically inoculated to the medium in each flask and cultured for 2 days under conditions of 23° C. and 210 rpm in a rotating shaker. 0.8 ml of a solution of the compound (X) dissolved at a concentration of 10 mg/ml in dimethyl sulfoxide was added to this culture solution in each flask, and the mixture was cultured again at 210 rpm at 23° C. for 3 days in a rotating shaker.

(2) Isolation of Terpenoid Derivative F

The behavior of terpenoid derivative F in this Example was monitored by HPLC under conditions given below.
column: Unison UK-C18
(4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 4.2 minutes (terpenoid derivative F).

To 2500 ml of the culture solution obtained in the paragraph (1), an equal amount of acetone was added, and the mixture was allowed to stand overnight at room temperature. Then, the mycelia were removed by suction filtration to obtain 4600 ml of a filtrate. To this filtrate, 2700 ml of ethyl acetate was added for liquid-liquid distribution to separate an organic layer containing the compound of interest. The organic layer was washed with saturated saline and dried over anhydrous sodium sulfate, and the solvent was evaporated off to obtain 762 mg of extracts containing terpenoid derivative F. These extracts were dissolved in 3.0 ml of dimethyl sulfoxide. A 0.4 ml of this solution was applied to an HPLC column (Unison US-C18; 20 mm in diameter×150 mm in length; manufactured by Imtakt Corp.) equilibrated in advance with solvents of 0.01% aqueous formic acid solution:acetonitrile containing 0.01% formic acid=45:55, followed by isocratic development for 10 minutes with solvents of 0.01% aqueous formic acid solution:acetonitrile containing 0.01% formic acid=45:55, then development in a linear gradient for 20 minutes up to a solvent ratio of 0.01% aqueous formic acid solution:acetonitrile containing 0.01% formic acid=10:90, and elution at a flow rate of 18.0 ml/min. The ultraviolet absorption of the compound of interest was detected at a wavelength λ=230 nm. A peak appearing at a retention time of 12.5 minutes (terpenoid derivative F) was separated 7 times. The fraction solutions were combined and concentrated under reduced pressure, and the obtained suspension was lyophilized to obtain 22.0 mg of terpenoid derivative F as a colorless powder.

Measurement Values of Physicochemical Properties of Terpenoid Derivative F
1) appearance: a colorless powdery substance
2) molecular formula: $C_{31}H_{40}N_2O_4$
3) molecular weight: 504 (measured by ESI mass spectrometry)
4) the accurate mass, $[M+H]^+$, measured by high-resolution LC-ESI mass spectrometry is as given below:
  found: 505.30551
  calculated: 505.30608
5) $^1$H-nuclear magnetic resonance spectra: the $^1$H-nuclear magnetic resonance spectra (500 MHz) measured with the signal of TMS defined as 0.00 ppm in deuterated chloroform are as given below:
  σ: 0.998 (3H, s), 1.001 (3H, s), 1.06 (3H, s), 1.14 (3H, s), 1.20 (3H, s), 1.30 (1H, t, J=13.5 Hz), 1.32 (3H, s), 1.36 (1H, dt, J=3.5 Hz, 12.5 Hz), 1.50 (3H, s), 1.54-1.58 (1H, m), 1.64-1.69 (1H, m), 1.68-1.70 (2H, m), 1.70-1.73 (1H, m), 1.74 (1H, dd, J=3.5 Hz, 13.5 Hz), 1.97-2.01 (1H, m), 2.00-2.03 (1H, m), 1.99-2.11 (2H, m), 2.07 (1H, brt, J=13.5 Hz), 2.80 (1H, dt, J=3.5 Hz, 13.5 Hz), 3.26 (1H, d, J=5.0 Hz), 3.45 (1H, dd, J=5.0 Hz, 12.0 Hz), 4.34 (1H, s), 6.14 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
  σ: 16.3 (q), 18.2 (t), 21.36 (q), 21.38 (q), 22.8 (q), 24.3 (q), 25.1 (t), 28.0 (q), 28.3 (t), 29.0 (q), 31.4 (t), 33.7 (d), 35.0 (t), 35.9 (s), 39.5 (t), 39.7 (s), 41.0 (s), 42.1 (s), 42.5 (d), 45.1 (s), 45.8 (s), 49.3 (d), 53.2 (s), 68.9 (d), 72.4 (d), 113.5 (s), 123.5 (s), 124.5 (d), 169.6 (s), 197.5 (s), 202.1 (s) ppm
7) high-performance liquid chromatography:
column: Unison UK-C18
  (4.6 mm in diameter×75 mm in length; manufactured by Imtakt Corp.)
solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 4.2 minutes.

Example 8

Production of Terpenoid Derivative G

[Formula 24]

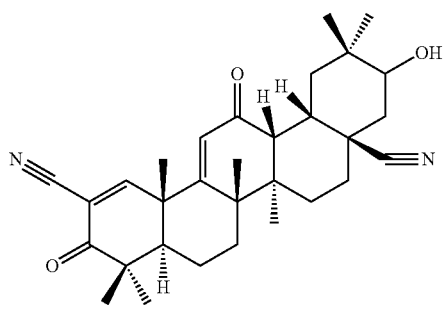

(VII)

Terpenoid Derivative G (1) Culture of Strain for Biotransformation of Genus *Chaetomium*

20 ml of a seed culture medium having the composition shown in Table 1 above was placed in each of ten 100-ml Erlenmeyer flasks, sterilized at 121° C. for 20 minutes, and then cooled to room temperature. 1 ml of a spore suspension of SANK 10312 was inoculated to the medium in each flask and cultured for 2 days under conditions of 23° C. and 210 rpm in a rotating shaker. (Hereinafter, the obtained culture solution is referred to as a "seed culture solution").

80 ml of a main culture medium having the composition shown in Table 2 above was placed in each of thirty-three 500-ml Erlenmeyer flasks, sterilized at 121° C. for 20 minutes, and then cooled to room temperature. 4 ml of the seed culture solution of SANK 10312 strain was aseptically inoculated to the medium in each flask and cultured for 2 days under conditions of 23° C. and 210 rpm in a rotating shaker. 0.8 ml of a solution of compound (X) dissolved at a concentration of 10 mg/ml in dimethyl sulfoxide was added to this culture solution in each flask, and the mixture was cultured again at 210 rpm at 23° C. for 3 days in a rotating shaker.

(2) Isolation of Terpenoid Derivative G

The behavior of terpenoid derivative G in this Example was monitored by HPLC under conditions given below.
column: Unison UK-C18
  (4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 3.7 minutes.

To 2500 ml of the culture solution obtained in paragraph (1), an equal amount of acetone was added, and the mixture was allowed to stand overnight at room temperature. Then, the mycelia was removed by suction filtration to obtain 4600 ml of a filtrate. To this filtrate, 2700 ml of ethyl acetate was added for liquid-liquid distribution to separate an organic layer containing the compound of interest. The organic layer was washed with saturated saline and dried over anhydrous sodium sulfate, and the solvent was evaporated to dryness to obtain 762 mg of extracts containing terpenoid derivative G. These extracts were dissolved in 3.0 ml of dimethyl sulfoxide. A 0.4 ml of this solution was applied to an HPLC column (Unison US-C18; 20 mm in diameter×150 mm in length; manufactured by Imtakt Corp.) equilibrated in advance with solvents of 0.01% aqueous formic acid solution:acetonitrile containing 0.01% formic acid=45:55, followed by isocratic development for 10 minutes with solvents of 0.01% aqueous formic acid solution:acetonitrile containing 0.01% formic acid=45:55, then development in a linear gradient for 20 minutes up to a solvent ratio of 0.01% aqueous formic acid solution:acetonitrile containing 0.01% formic acid=10:90, and elution at a flow rate of 18.0 ml/min. The ultraviolet absorption of the compound of interest was detected at a wavelength λ=230 nm. A peak appearing at a retention time of 9.4 minutes (terpenoid derivative G) was separated 7 times. The fraction solutions were combined and concentrated under reduced pressure, and the obtained suspension was lyophilized to obtain 30.4 mg of terpenoid derivative G as a colorless powder.

Measurement Values of Physicochemical Properties of Terpenoid Derivative G 1) appearance: a colorless powdery substance
2) molecular formula: $C_{31}H_{40}N_2O_3$
3) molecular weight: 488 (measured by ESI mass spectrometry)
4) the accurate mass, $[M+H]^+$, measured by high-resolution LC-ESI mass spectrometry is as given below:
   found: 489.31073
   calculated: 489.31117
5) $^1$H-nuclear magnetic resonance spectra: the $^1$H-nuclear magnetic resonance spectra (500 MHz) measured with the signal of TMS defined as 0.00 ppm in deuterated chloroform are as given below:
   σ: 0.996 (3H, s), 0.997 (3H, s), 0.998 (3H, s), 1.19 (3H, s), 1.27 (3H, s), 1.28 (1H, t, J=14.0 Hz), 1.36 (1H, dt, J=2.5 Hz, 13.0 Hz), 1.53 (3H, s), 1.56 (3H, s), 1.60-1.64 (1H, m), 1.63-1.69 (1H, m), 1.70-1.74 (1H, m), 1.71 (1H, dd, J=3.5 Hz, 14.0 Hz), 1.78 (1H, dd, J=3.0 Hz, 11.0 Hz), 1.82-1.86 (2H, m), 1.99-2.02 (1H, m), 1.99-2.10 (2H, m), 2.08 (1H, brt, J=12.0 Hz), 2.79 (1H, dt, J=3.5 Hz, 13.5 Hz), 3.25 (1H, d, J=5.0 Hz), 3.45 (1H, dd, J=5.0 Hz, 11.5 Hz), 6.02 (1H, s), 8.03 (1H, s) ppm
6) $^{13}$C-nuclear magnetic resonance spectra: the $^{13}$C-nuclear magnetic resonance spectra (125 MHz) measured with the signal of TMS defined as 0.00 ppm in deuterated chloroform are as given below:
   σ: 16.3 (q), 18.2 (t), 21.4 (q), 21.5 (q), 24.9 (q), 25.1 (t), 26.7 (q), 27.0 (q), 28.1 (t), 29.0 (q), 31.7 (t), 33.6 (d), 34.9 (t), 35.9 (s), 39.5 (t), 39.6 (s), 42.1 (s), 42.6 (s), 45.0 (s), 45.9 (s), 47.8 (d), 49.3 (d), 72.4 (d), 114.3 (s), 114.7 (s), 123.5 (s), 123.7 (d), 165.2 (d), 169.4 (s), 196.3 (s), 197.6 (s) ppm
7) high-performance liquid chromatography:
column: Unison UK-C18
  (4.6 mm in diameter×75 mm in length; manufactured by Imtakt Corp.)
Solvent:
  A: 10 mM aqueous ammonium formate solution containing 0.01% formic acid
  B: acetonitrile containing 0.01% formic acid
  A/B=equilibration with 5/5 followed by linear gradient for 7 minutes up to A/B=1/9
flow rate: 1.0 ml/min
temperature: 40° C.
detection: ultraviolet absorption λ230 nm
retention time: 3.7 minutes.

Test Example 1

<Effect of Inducing Nrf2 Target Gene (In Vitro)>

The Hmox1 gene was used as the Nrf2 target gene. The expression level of the Hmox1 gene induced by the addition of a test compound to ARPE-19 cells (human retinal pigment epithelium cell line, ATCC, catalog No. CRL-2302) was measured to examine the effect of inducing the Hmox1 gene by the test compound. The test compound was terpenoid derivative B of the present invention obtained in Example 1 and CDDO-Me as Comparative Example.

The ARPE-19 cells were cultured (5% $CO_2$, 37° C.) using a DMEM/F12 (Life Technologies Japan Ltd., catalog No. 11330-032) mixed medium containing 10% inactivated FBS. The medium contained 100 units/mL (final concentration) penicillin and 100 μg/mL (final concentration) streptomycin. The ARPE-19 cells were seeded at 60000 cells/well in a 24-well plate. The amount of the medium was 500 Approximately 24 hours later, the medium was replaced with a medium containing terpenoid derivative B of the present invention obtained in Example 1 or CDDO-Me, and the culture was continued. Approximately 6 hours later, mRNA was collected from the ARPE-19 cells using an extraction kit (manufactured by Qiagen N.V., RNeasy Mini Kit, catalog No. 74106). From the obtained mRNA, cDNA was prepared using a cDNA synthesis kit (manufactured by GE Healthcare Life Sciences, First-Strand cDNA Synthesis Kit). The obtained cDNA was amplified using a reagent (manufactured by Applied Biosystems, Inc., TaqMan® Gene Expression Master Mix (catalog No. 4369016)) and a probe, and subjected to real-time quantitative PCR (Real-time PCR HT7900 manufactured by Applied Biosystems, Inc. was used).

When the concentration of the test compound was 0 nM, the expression level of the Hmox1 gene was defined as 1.0±0.0. The expression level of the Hmox1 gene at each concentration of the test compound was indicated as a relative value. The results are shown in Table 3 below. Each group consisted of 3 wells and was indicated by a mean and standard deviation.

TABLE 3

| Hmox1 gene expression level | | |
|---|---|---|
| Test compound concentration (nM) | CDDO-Me | Terpenoid derivative B |
| 0 | 1.0 ± 0.0 | 1.0 ± 0.0 |
| 0.00001 | 1.1 ± 0.0 | 1.3 ± 0.0 |
| 0.001 | 1.0 ± 0.1 | 0.9 ± 0.1 |
| 0.03 | 1.4 ± 0.0 | 5.4 ± 0.1 |
| 0.3 | 1.4 ± 0.1 | 6.1 ± 0.5 |
| 3 | 2.1 ± 0.3 | 10.4 ± 1.5 |
| 30 | 12.2 ± 2.6 | 20.8 ± 1.9 |

As a result of analyzing these results using medical statistical analysis software (manufactured by GraphPad Software, Inc., Prism (Ver. 5)), the concentrations at which the expression level of the Hmox1 gene was increased 2-fold and 5-fold were 2.5 nM and 11 nM for CDDO-Me, and 0.00091 nM and 0.12 nM for terpenoid derivative B of the present invention. The activity ratios of terpenoid derivative B of the present invention to CDDO-Me were 2747 times and 92 times.

Test Example 2

<Effect of Cytoprotective Action>

The peroxide tert-butyl hydroperoxide (t-BHP) is known to cause oxidative stress-dependent cell injury (Chem Biol Interact 2009; 181: 366- and Food Chem Toxicol 2011; 49: 2081).

The degree to which the addition of a test compound suppressed decrease in the number of live cells caused by the addition of t-BHP to ARPE-19 cells (human retinal pigment epithelium cell line, ATCC, catalog No. CRL-2302) was measured to examine the effect of cytoprotective action. The test compound was terpenoid derivative B of the present invention obtained in Example 1 and CDDO-Me as Comparative Example.

ARPE-19 cells were cultured (5% $CO_2$, 37° C.) using a DMEM/F12 (Life Technologies Japan Ltd., catalog No. 11330-032) mixed medium containing 10% inactivated FBS. The medium contained 100 units/mL (final concentration) penicillin and 100 μg/mL (final concentration) streptomycin.

The ARPE-19 cells were seeded at 10000 cells/well in a 96-well plate. The amount of the medium was 100 μL. Approximately 6 hours later, the medium was replaced with a medium containing terpenoid derivative B of the present invention obtained in Example 1 or CDDO-Me. After culture for approximately 16 hours, the number of live ARPE-19 cells was measured (Cell Counting Kit-8 (catalog No. CK01) manufactured by Dojindo Laboratories was used). Then, the medium was replaced with medium containing 300 μM t-BHP (manufactured by Sigma-Aldrich Corp., catalog No. 46665) and further containing terpenoid derivative B of the present invention obtained in Example 1 or CDDO-Me. Approximately 6 hours after the addition of t-BHP, the number of live ARPE-19 cells was measured.

The number of live cells in medium containing neither t-BHP nor the test compound was defined as 100%. The number of live cells in medium containing 300 μM t-BHP and each concentration of the test compound was indicated by percentage. The results are shown in Table 4 below. Each group consisted of 3 wells and was indicated as a mean and standard deviation.

TABLE 4

| Number of live cells (percentage) | | | |
|---|---|---|---|
| t-BHP (μM) | Test compound concentration (nM) | CDDO-Me (%) | Terpenoid derivative B (%) |
| 0 | 0 | 100 ± 0.0 | 100 ± 0.0 |
| 300 | 0 | 61.6 ± 3.0 | 61.6 ± 3.0 |
| 300 | 0.03 | 61.8 ± 2.0 | 90.3 ± 3.9 |
| 300 | 0.3 | 56.7 ± 1.2 | 99.0 ± 10.0 |
| 300 | 3 | 74.3 ± 1.4 | 119.7 ± 5.7 |
| 300 | 30 | 84.7 ± 4.8 | 114.3 ± 9.5 |
| 300 | 300 | 76.1 ± 2.8 | 111.2 ± 3.8 |

The addition of t-BHP decreased cell activity to 61.6%. The addition of CDDO-Me did not completely suppress the decrease in the number of live cells, whereas the addition of the compound completely suppressed such decrease.

Test Example 3

<Effect of Inducing Nrf2 Target Gene (In Vivo)>

The Nqo1 gene was used as the Nrf2 target gene.

Respective suspensions of terpenoid derivative B of the present invention obtained in Example 1 and CDDO-Me were prepared using 0.5 w/v % methylcellulose solution 400 cP (Wako Pure Chemical Industries, Ltd., catalog No. 133-14255) as a solvent. Each suspension was orally administered once a day for 12 consecutive days at a dose of 1, 3, or 10 mg/kg with administration volume of 10 mL/kg to each C57 Black 6 mouse (Charles River Laboratories Japan, Inc., male, 8 weeks old at the time of receipt, 10 weeks old at the start of the experiment). On the next day of the final administration, the mouse was euthanized, and the kidney was sampled. From the sampled kidney, mRNA was collected using an extraction kit (manufactured by Qiagen N.V., RNeasy Mini Kit, catalog No. 74106). From the obtained mRNA, cDNA was prepared using a cDNA synthesis kit (manufactured by GE Healthcare Life Sciences, First-Strand cDNA Synthesis Kit). The obtained cDNA was amplified using a reagent (manufactured by Applied Biosystems, Inc., TaqMan® Gene Expression Master Mix (catalog No. 4369016)) and a probe, and subjected to real-time quantitative PCR (Real-time PCR HT7900 manufactured by Applied Biosystems, Inc. was used). Table 5 shows results of induction when the expression level of the Nqo1 gene in the kidney of a group given only the solvent was defined as 1. Each group consisted of 6 mice and was indicated as a mean and standard deviation.

TABLE 5

Nqo1 gene expression level

| Dose (mg/kg) | CDDO-Me | Terpenoid derivative B |
|---|---|---|
| 0 | 1.0 ± 0.1 | 1.0 ± 0.1 |
| 1 | 1.0 ± 0.0 | 1.2 ± 0.1 |
| 3 | 1.0 ± 0.1 | 1.8 ± 0.2 |
| 10 | 1.0 ± 0.1 | 2.3 ± 0.2 |

Terpenoid derivative B of the present invention obtained in Example 1 was confirmed to induce the Nqo1 gene at a dose of 1 mg/kg, whereas CDDO-Me was not confirmed to induce the Nqo1 gene.

Test Example 4

<Cytotoxicity>

ARPE-19 cells (human retinal pigment epithelium cell line, ATCC, catalog No. CRL-2302) were cultured (5% $CO_2$, 37° C.). A DMEM/F12 (Life Technologies Japan Ltd., catalog No. 11330-032) mixed medium containing 10% inactivated FBS was used. The medium contained 100 units/mL (final concentration) penicillin and 100 µg/mg (final concentration) streptomycin.

The ARPE-19 cells were seeded at 5000 cells/well in a 96-well plate. The amount of the medium was 50 µL. Approximately 3 hours later, 50 µL of a medium containing CDDO-Me or each of terpenoid derivatives A to H was added thereto, followed by culture for approximately 16 hours. Then, cytotoxicity was evaluated using LDH-Cytotoxic Test (Wako Pure Chemical Industries, Ltd., catalog No. 299-50601). The evaluation method followed the attached document. Each group consisted of 3 wells and was indicated as cytotoxicity at the concentration of 10 µM. The means thereof were 43% for CDDO-Me, 2% for terpenoid derivative A, 2% for terpenoid derivative B, 2% for terpenoid derivative C, 1% for terpenoid derivative D, 2% for terpenoid derivative E, 3% for terpenoid derivative F, 3% for terpenoid derivative G, and 1% for terpenoid derivative H. Terpenoid derivatives A to H were low in cytotoxicity as compared with CDDO-Me.

Test Example 5

<NQO1 Assay>

Hepa1c1c7 cells (mouse hepatic cell line, ATCC, catalog No. CRL-2026) were cultured (5% $CO_2$, 37° C.). A DMEM (Life Technologies Japan Ltd., catalog No. 11965-092) medium also containing 10% inactivated FBS was used. The medium contained 100 units/mL (final concentration) penicillin and 100 µg/mg (final concentration) streptomycin. The NQO1 assay was conducted according to previous reports (Anal Biochem 1998; 169: 328-; and Methods Enzymol 2004; 382: 243-).

The Hepa1c1c7 cells were seeded at 10000 cells/well in a 96-well plate. The amount of the medium was 100 µL. Approximately 24 hours later, the medium was replaced with a medium containing CDDO-Me or each of terpenoid derivatives A to G, followed by further culture for approximately 48 hours. A lysis solution (a solution containing 2 mM EDTA and 0.8% digitonin), a reaction solution (a solution containing 0.025 M of tris-HCl, 0.067% of albumin, 0.01% of Tween-20, 2 U/mL of glucose-6-phosphate dehydrogenase, 5 µM of flavin adenine dinucleotide, 1 µM of glucose-6-phosphate, 30 µM of nicotinamide adenine dinucleotide phosphate, 0.03% of 3-(4, 5-dimethyl-2-thiazolyl)-2,5-diphenyltetrazolium bromide (MTT), and 50 µM of menadione), and a stop solution (a solution containing 0.3 mM dicumarol and 5 mM potassium dihydrogen phosphate, pH 7.4) were prepared. After removal of the medium, 50 µL of the lysis solution was added thereto, and the mixture was left standing at 37° C. for 10 minutes. The reaction mixture was further shaken at room temperature for 10 minutes.

Two hundred µL of the solution was added thereto, and the mixture was left standing at room temperature for 5 minutes. Fifty µL of the stop solution was added thereto, and the absorbance at 490 nm was measured.

The test results were analyzed using Prism (GraphPad Software, Inc., Ver. 5) to calculate the CD value of the concentration at which the activity of NQO1 was increased 2-fold. Each group consisted of 3 wells and indicated as a mean of CD values.

The CD values were 1.0 nM for CDDO-Me, 1.3 nM for terpenoid derivative A, 0.3 nM for terpenoid derivative B, 0.4 nM for terpenoid derivative C, 0.9 nM for terpenoid derivative D, 2.1 nM for terpenoid derivative E, 0.1 nM for terpenoid derivative F, and 0.1 nM for terpenoid derivative G.

Test Example 6

<Inhibitory Effect on Oxygen-Induced Retinopathy in Rat (In Vivo)>

SD rat newborns (Charles River Laboratories Japan, Inc., pregnant rats were received) were used in the experiment. From the ages of 1 day to 12 days, the newborns were raised under approximately 80% oxygen with the mother rats. The newborns were raised under the atmosphere from the age of 13 days. A suspension of the terpenoid derivative B was prepared using a 0.5 w/v % methylcellulose solution 400 cP (Wako Pure Chemical Industries, Ltd., catalog No. 133-14255) as a solvent. The suspension was orally administered once a day from the ages of 11 days to 17 days, a total of seven times, at a dose of 0.03, 0.1, or 0.3 mpk with administration volume of 10 mL/kg. On the next day of the final concentration, the newborn rats were euthanized, and the retina was sampled. The pathological condition of the retina was scored according to the literature (Invest Ophthalmol Vis Sci 2000; 41: 887-). The results are shown in Table 6. Each group consisted of 14 to 30 eyes and was indicated as a mean and standard deviation.

TABLE 6

| Pathological condition of retina in oxygen-induced retinopathy in rat | | |
|---|---|---|
| Oxygen load | Dose (mg/kg) | Score of terpenoid derivative B |
| Absent | 0 | 0.00 ± 0.00 |
| Present | 0 | 4.00 ± 0.44 |
| Present | 0.03 | 3.93 ± 0.79 |
| Present | 0.1 | 3.54 ± 0.48 |
| Present | 0.3 | 2.57 ± 0.35 |

Terpenoid derivative B suppressed the score of the pathological condition of the retina in a dose-dependent manner.

Formulation Example 1

<Tablet>

| | |
|---|---|
| Terpenoid derivative B of the present invention | 30 mg |
| Lactose | 118 mg |
| Corn starch | 50 mg |
| Magnesium stearate | 2 mg |
| Total | 200 mg |

Formulation Example 2

<Eye Drop>

| | |
|---|---|
| Terpenoid derivative B of the present invention | 300 mg |
| Sodium dihydrogen phosphate (pH adjuster) | 1 ml |
| Sodium chloride | q.s. |
| Sterile purified water | q.s. |
| Total | 100 ml |

The invention claimed is:

1. A terpenoid derivative represented by the following formula (II):

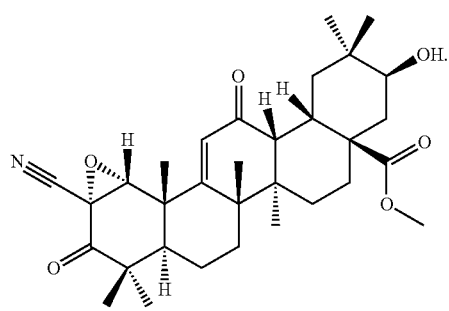

(II)

2. A method for producing a compound according to claim 1, comprising using a compound represented by the following formula (VIII):

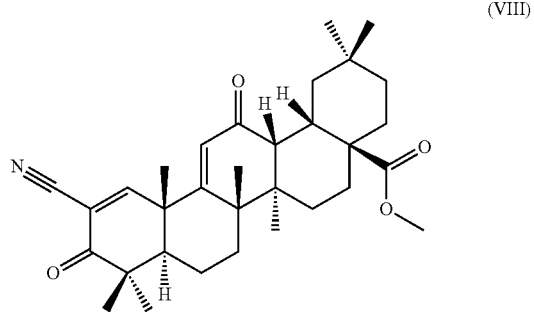

(VIII)

as a substrate, culturing this compound in a medium together with a strain for transformation of the genus *Chaetomium* capable of transforming the compound to the compound according to claim 1, and collecting the compound according to claim 1 from the cultures.

3. The method for producing a compound according to claim 2, wherein the strain for transformation is a *Chaetomium globosum* SANK 10312 strain (Deposition No. NITE BP-1486) belonging to the genus *Chaetomium*.

4. A method for producing a compound according to claim 1, comprising using a compound represented by the following formula (VIII):

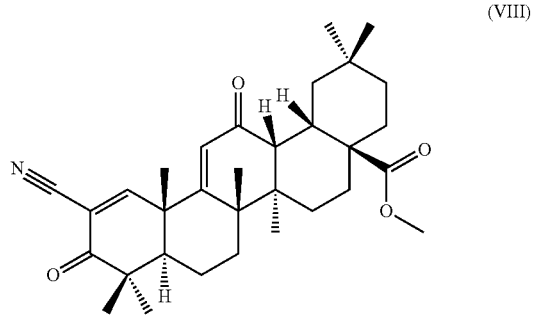

(VIII)

as a substrate, culturing this compound in a medium together with a strain for transformation of the genus *Mucor* capable of transforming the compound to the compound according to claim 1, and collecting the compound according to claim 1 from the cultures.

5. The method for producing a compound according to claim 4, wherein the strain for transformation is a *Mucor hiemalis* f *hiemalis* SANK 10612 strain (Deposition No. NITE BP-1488) belonging to the genus *Mucor*.

6. A medicament comprising a terpenoid derivative according to claim 1 as an active ingredient.

* * * * *